United States Patent [19]

Scarborough et al.

[11] Patent Number: 5,047,397
[45] Date of Patent: Sep. 10, 1991

[54] LINEAR ANALOGS OF ATRIAL NATRIURETIC PEPTIDES

[75] Inventors: Robert M. Scarborough, Hayward; John A. Lewicki, Los Gatos; Lorin K. Johnson, Pleasanton, all of Calif.

[73] Assignee: California Biotechnology Inc., Mountain View, Calif.

[21] Appl. No.: 285,916

[22] Filed: Dec. 16, 1988

Related U.S. Application Data

[63] Continuation-in-part of Ser. No. 237,299, Aug. 26, 1988, abandoned, which is a continuation-in-part of Ser. No. 138,893, Dec. 24, 1987, abandoned, which is a continuation-in-part of Ser. No. 921,360, Oct. 28, 1986, abandoned, which is a continuation-in-part of Ser. No. 904,091, Sep. 4, 1986, abandoned, which is a continuation-in-part of Ser. No. 868,312, May 28, 1986, Pat. No. 4,757,048, which is a continuation-in-part of Ser. No. 795,220, Nov. 5, 1985, abandoned, Ser. No. 168,661, Mar. 16, 1988, Pat. No. 4,804,650, Continuation of Ser. No. 921,360, , and a continuation-in-part of Ser. No. 904,091, , Ser. No. 868,312, , and a continuation-in-part of Ser. No. 795,220.

[51] Int. Cl.$^5$ .......................... C07K 7/06; C07K 7/08; C07K 7/10; A61K 37/02
[52] U.S. Cl. ....................... 514/12; 530/350; 530/324; 530/326; 530/330; 514/13; 514/14; 514/17
[58] Field of Search ............... 530/324, 325, 326, 327, 530/328, 329, 330, 350; 514/17, 16, 15, 14, 13, 12

[56] References Cited

U.S. PATENT DOCUMENTS 4,496,544 1/1985 Needleman .
4,508,712 4/1985 Needleman .
4,804,650 2/1989 Lewicki et al. ...................... 530/330

FOREIGN PATENT DOCUMENTS 0271041 12/1986 European Pat. Off. .
0223141 5/1987 European Pat. Off. .
0249169 12/1987 European Pat. Off. .
0269220 6/1988 European Pat. Off. .
0356124 2/1990 European Pat. Off. .
WO88/03537 5/1988 PCT Int'l Appl. .

OTHER PUBLICATIONS

Schiller, P. W., Biochem. and Biophys. Res. Commun., 131(3):1056-1062, Sep. 1985.
Nakoo, K., Horumon to Rinsho, 33(4):365-370, 1985.
Kiso, Y., J. Protein Chemistry, 6(2):147-162, Apr. 16, 1987.
De Bold et al., Life Sciences, 28:89-94 (1981).
Currie et al., Science, 221:71-73 (1983).
Currie et al., Science, 223:67-69 (1984).
Flynn et al., Biochem. Biophys. Res. Commun., 117(3):859-865 (1983).
Garcia, Experientia, 38:1071-1073 (1982).
Kangawa et al., Biochem. Biophys. Res. Commun., 118(1):131-139 (1984).
Kangawa et al., Biochem. Biophys. Res. Commun., 119(3):933-940 (1984).

Primary Examiner—Lester L. Lee
Assistant Examiner—Susan M. Perkins
Attorney, Agent, or Firm—Irell & Manella

[57] ABSTRACT

Compounds and compositions comprising synthetic analogs of Atrial Natriuretic Peptides are provided, together with methods for their production and use as natriuretics, diuretics and/or vasodilators, or as intermediates for or modulators of such useful compounds or of native Atrial Natriuretic Peptides.

20 Claims, 41 Drawing Sheets

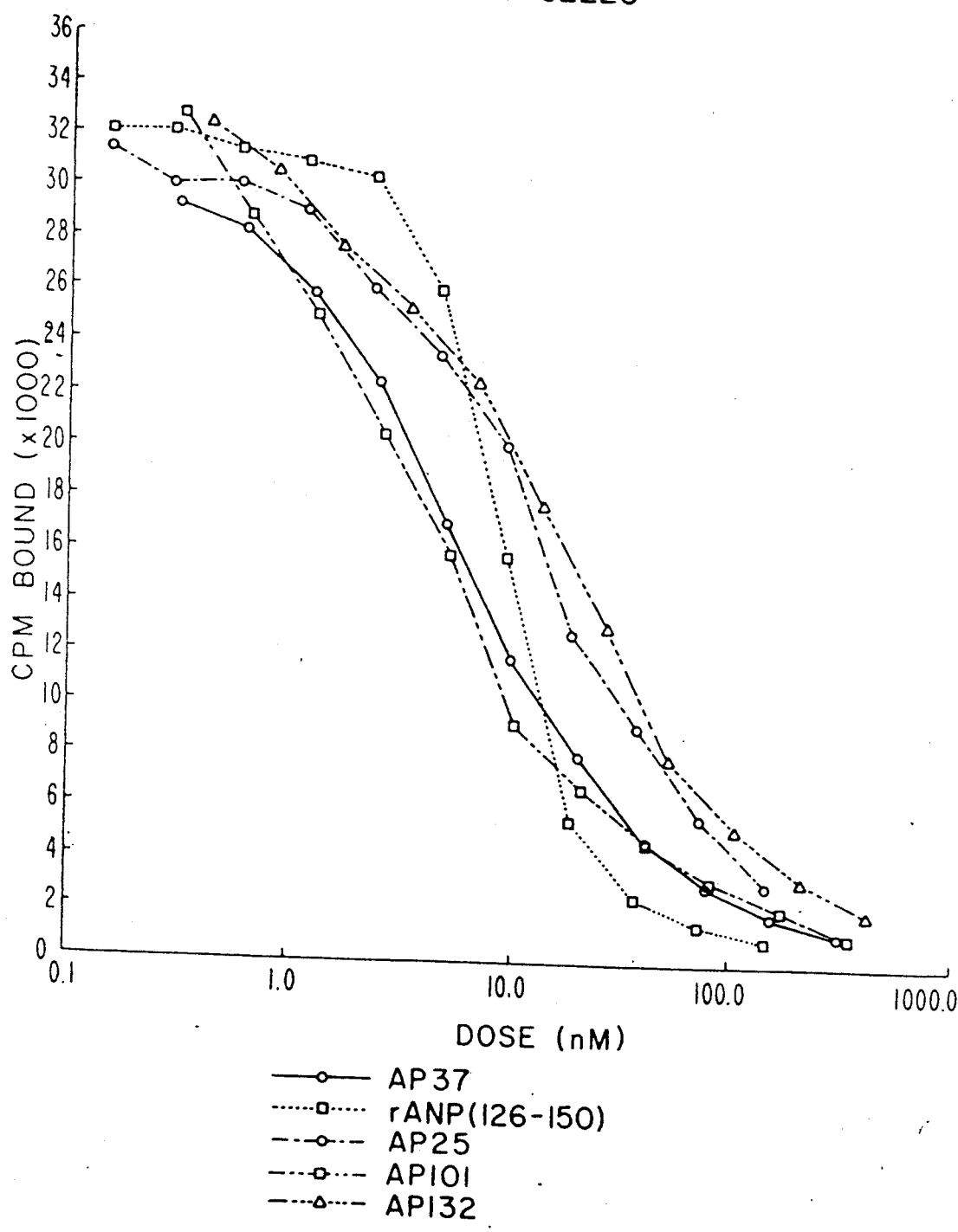
FIG_2_
BINDING OF ATRIAL NATRIURETIC PEPTIDE ANALOGS TO BASM CELLS

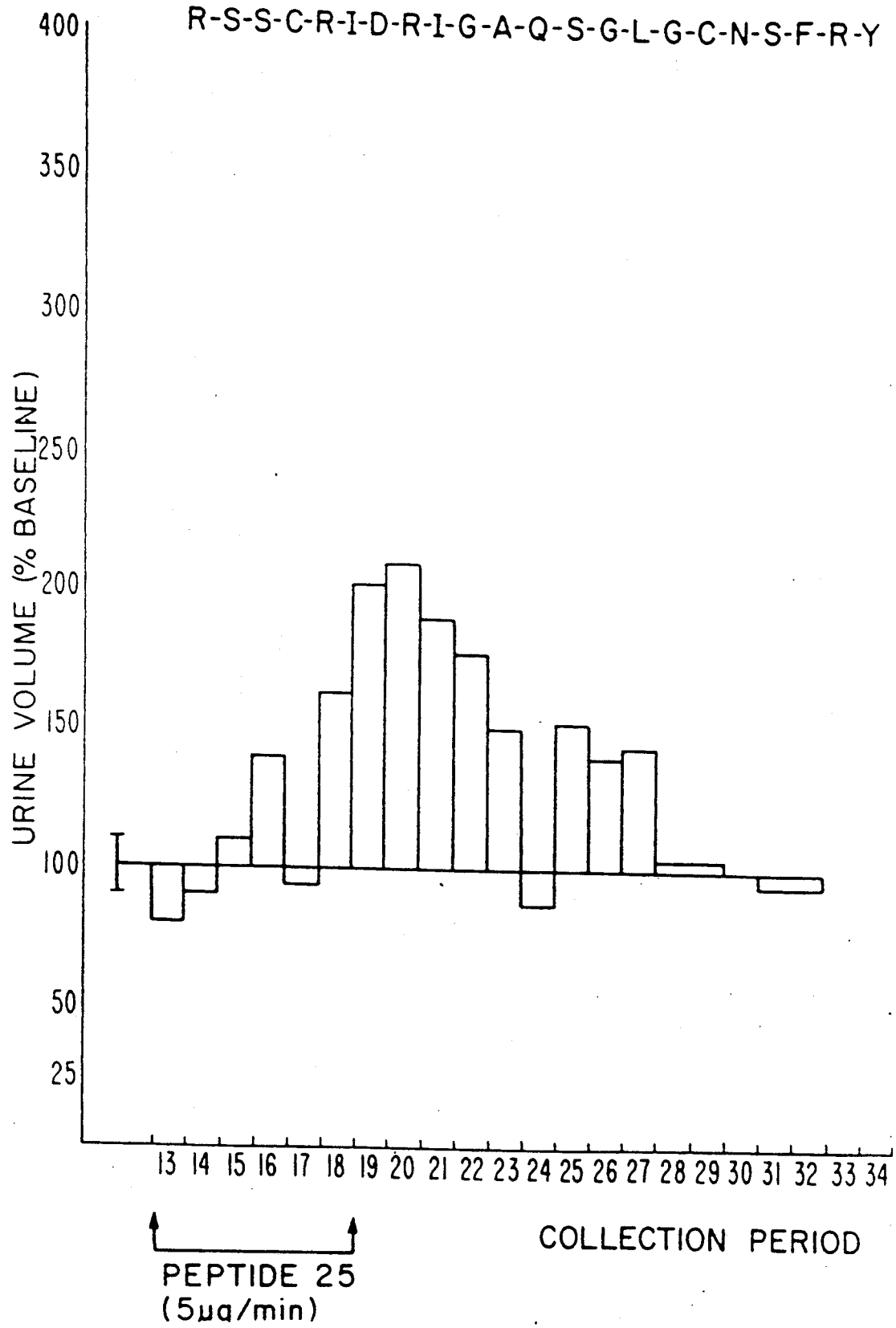

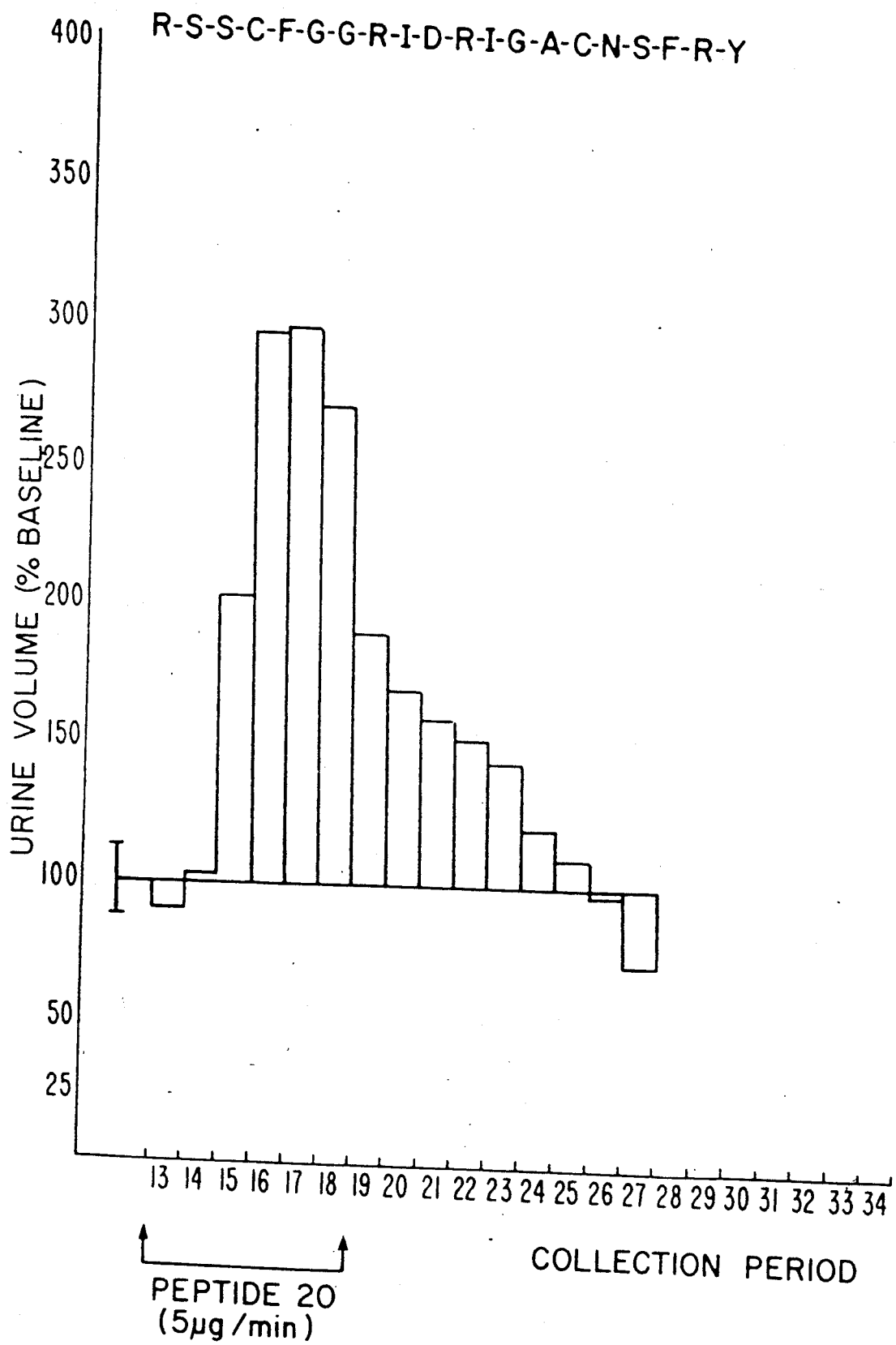

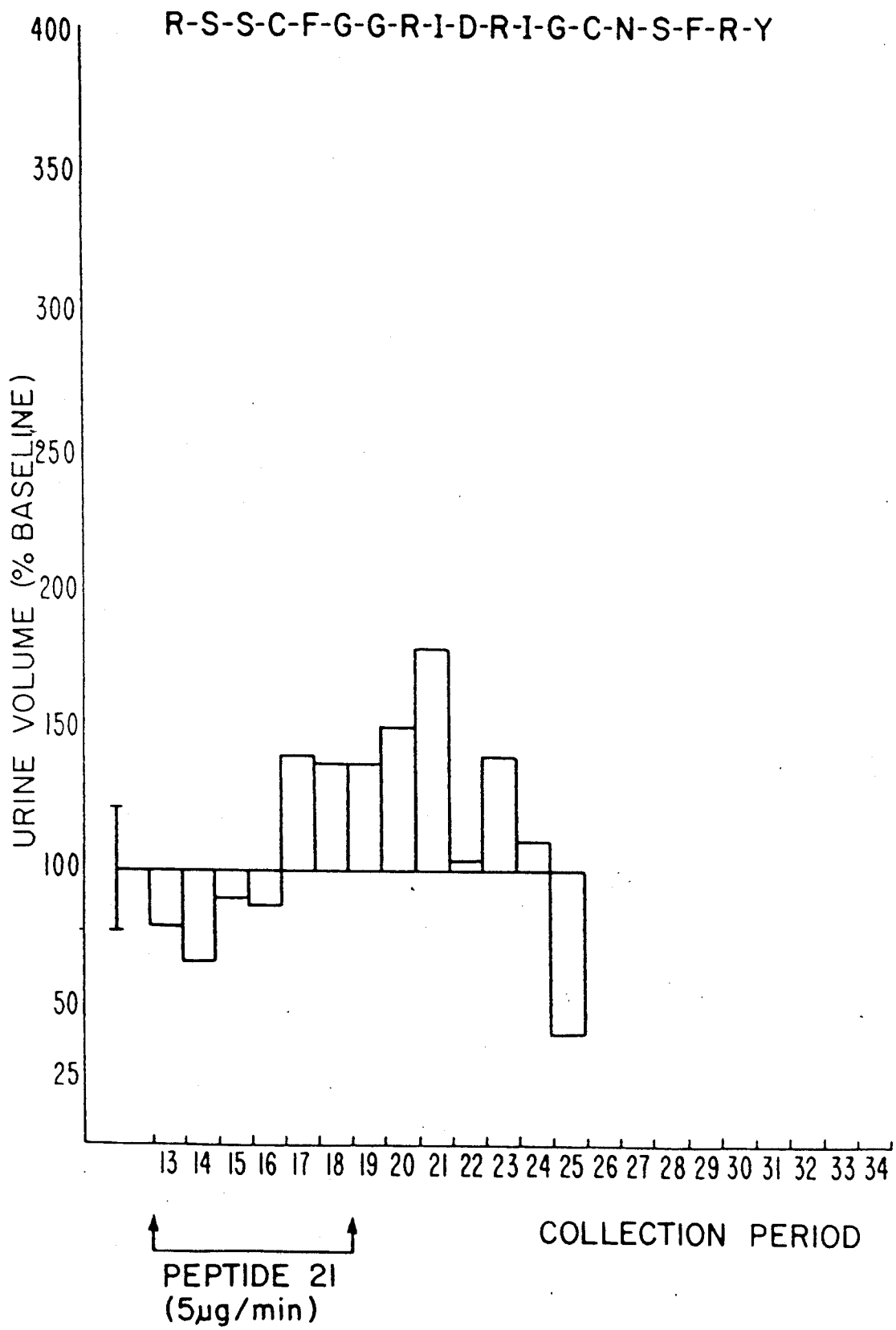

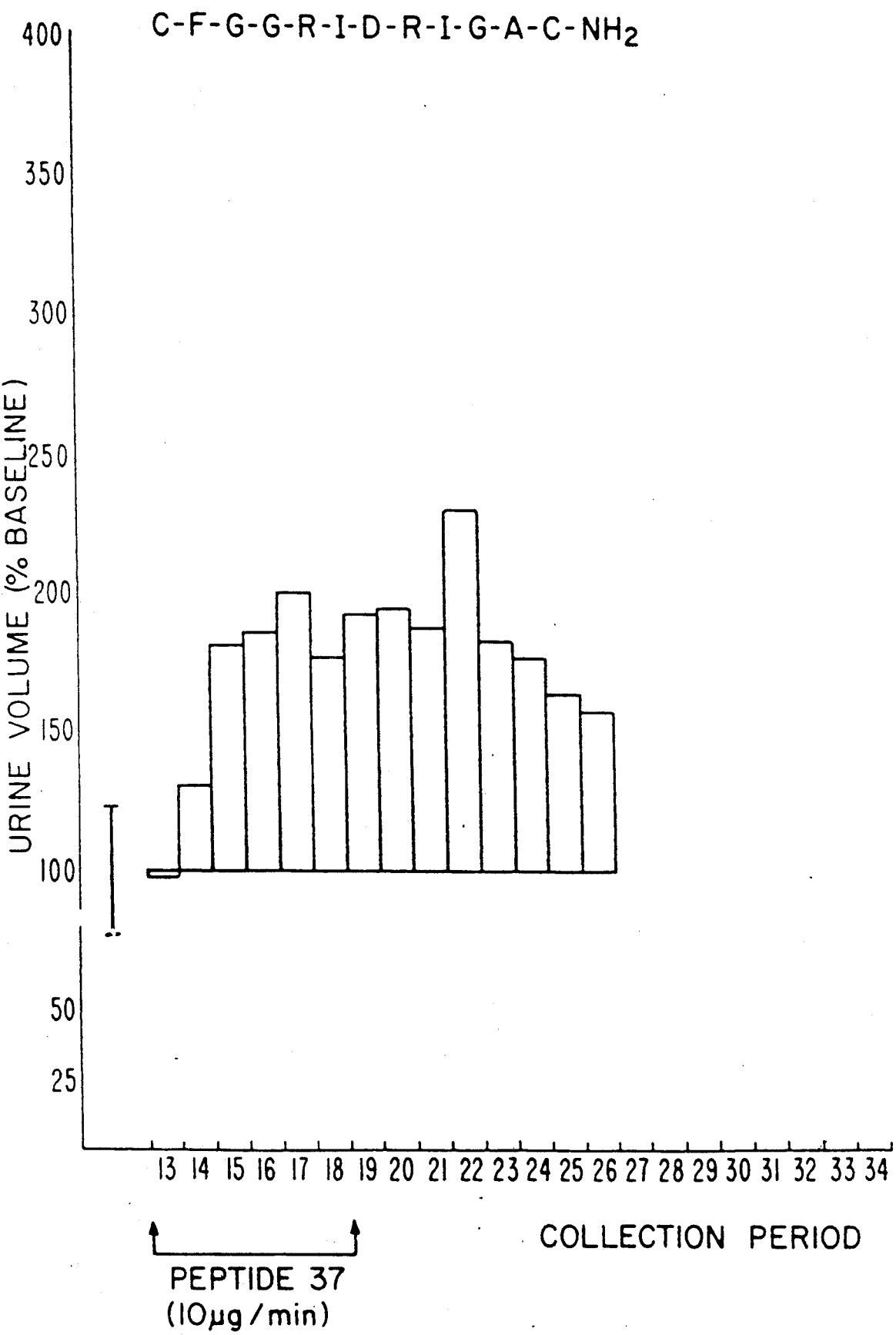

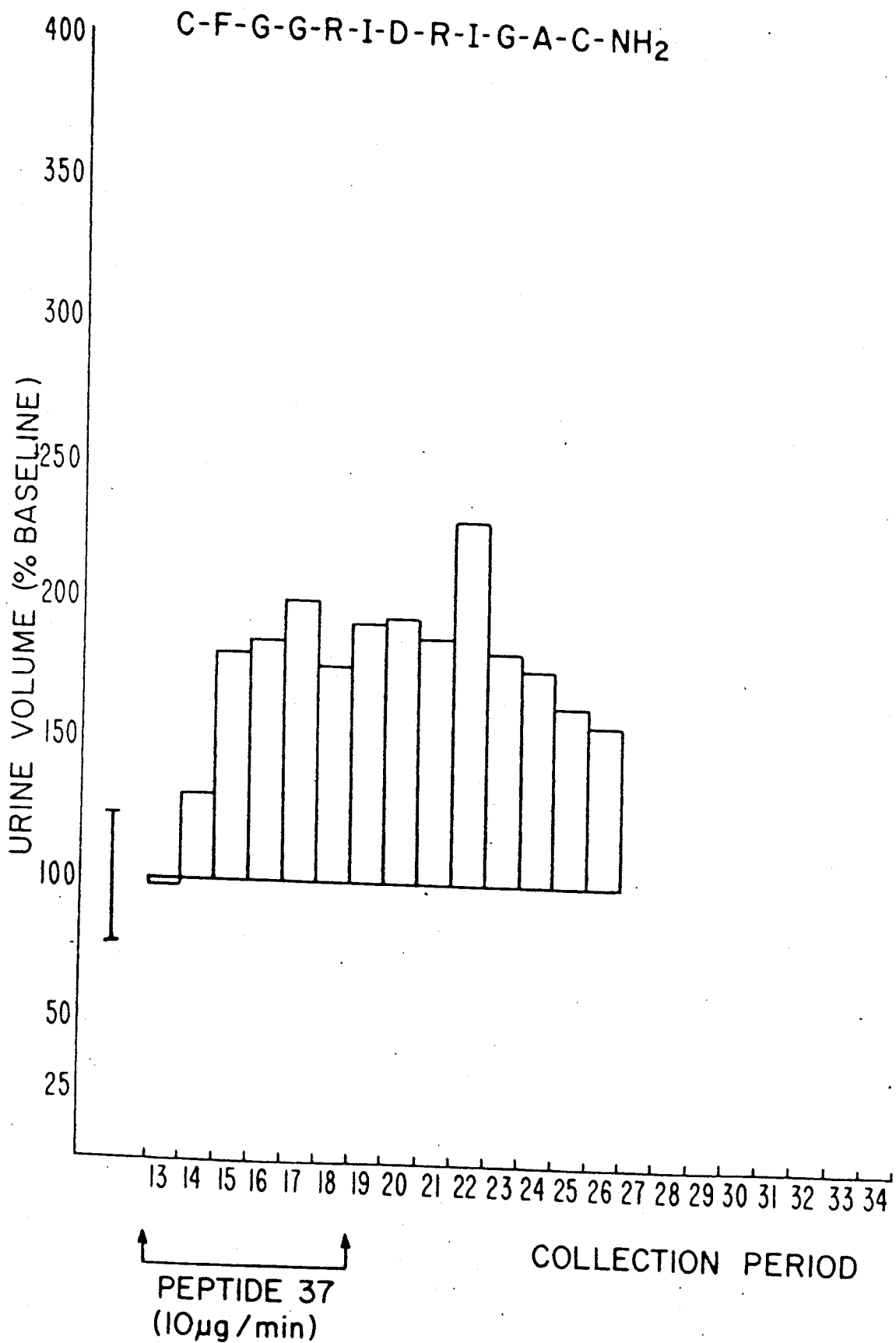

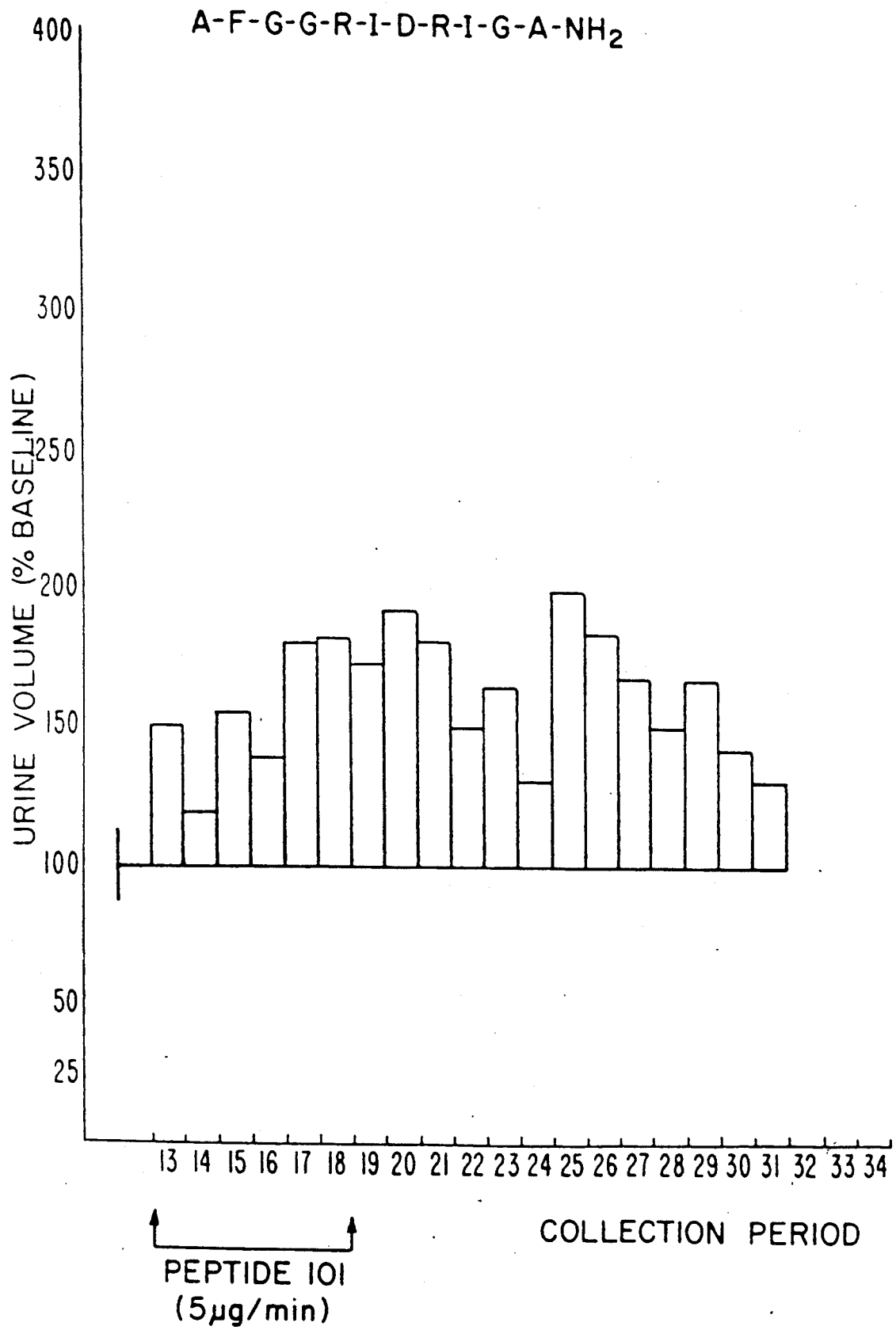

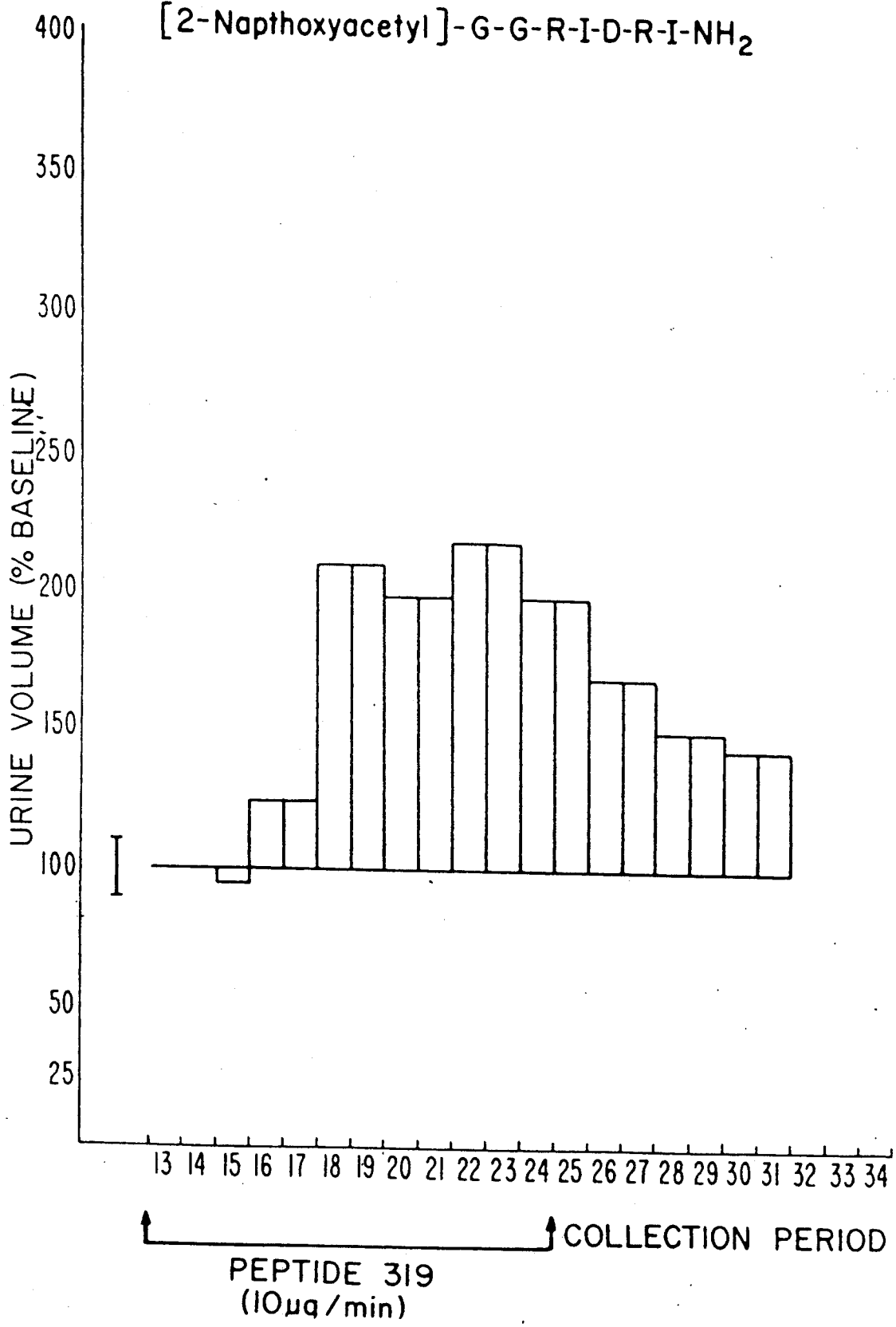

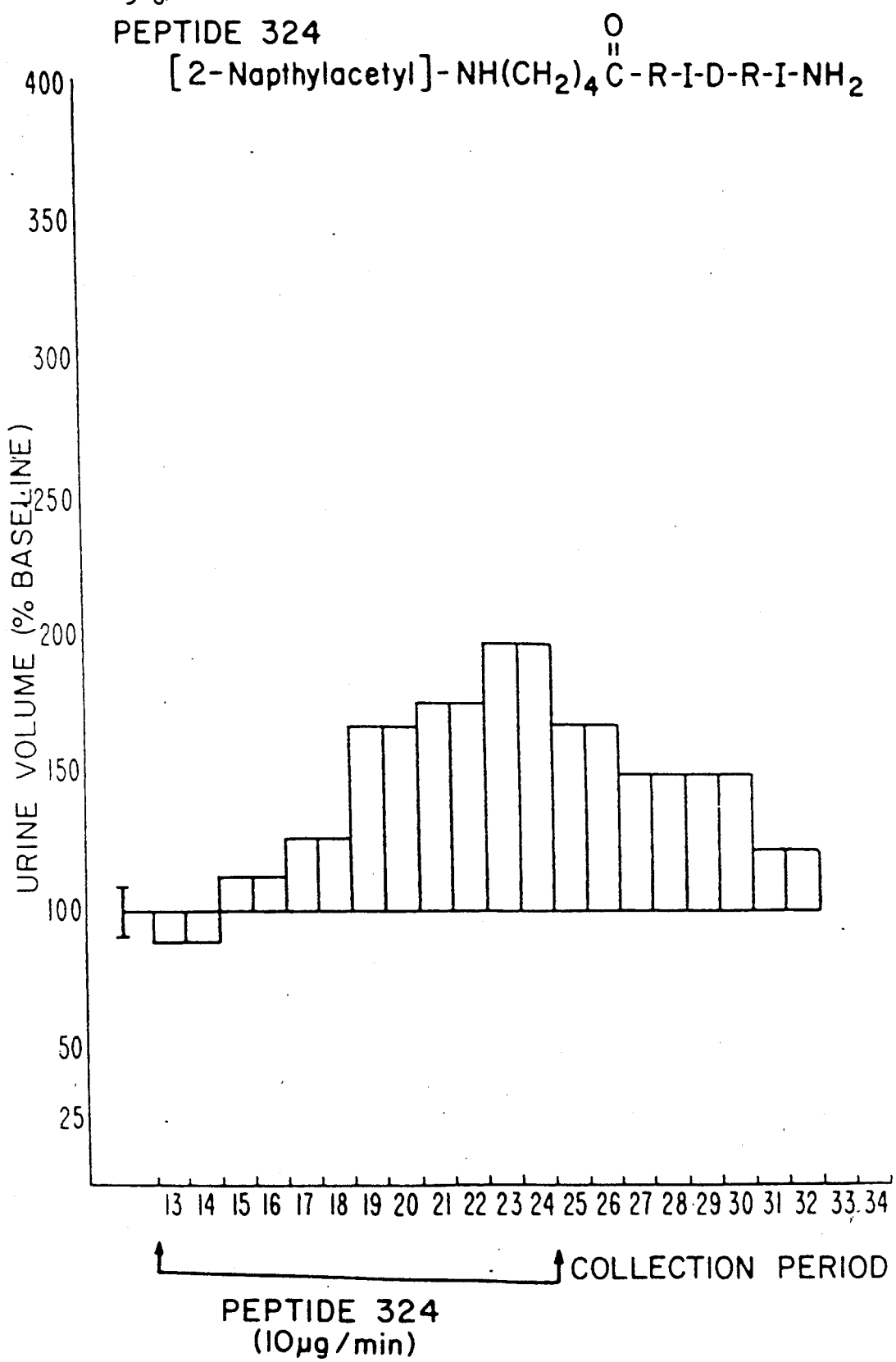

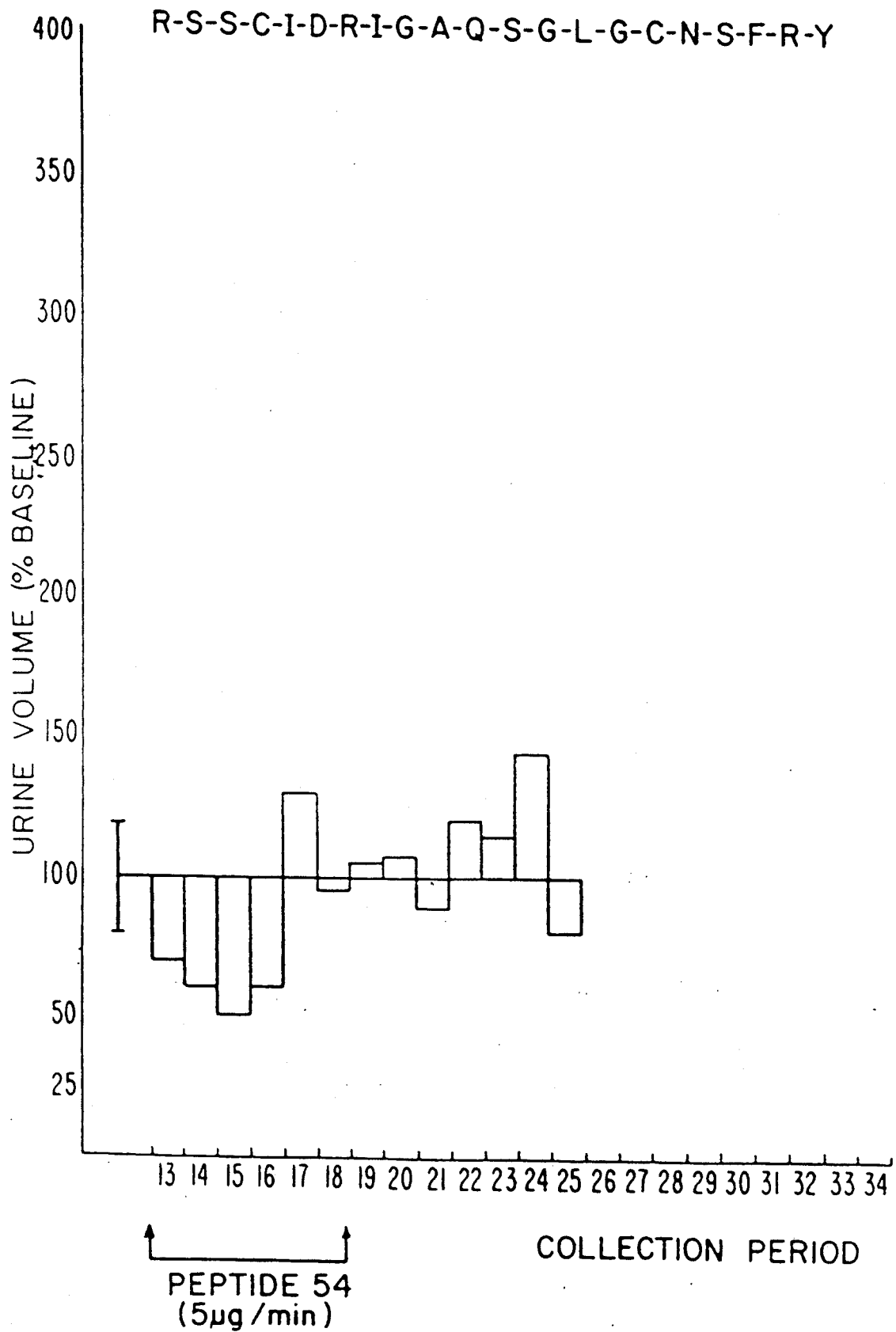

\* Indicates amino acid analysis has been performed.

\* AP100    A-F-G-G-R-I-D-R-I-G-A-A-NH$_2$

\* AP101    A-F-G-G-R-I-D-R-I-G-A-NH$_2$

\* AP102    A-F-G-G-R-I-D-R-I-G-NH$_2$

\* AP103    A-F-G-G-R-I-D-R-I-NH$_2$

\* AP104    F-G-G-R-I-D-R-I-G-A-A-NH$_2$

AP118    A-F-G-G-R-M-D-R-I-G-NH$_2$

\* AP119    F-G-G-R-I-D-R-I-NH$_2$

\* AP122    F-G-G-R-I-D-R-I-G-NH$_2$

\* AP126    F-G-G-R-I-D-R-I-G-A-NH$_2$

\* AP130    (desNH$_2$-F)-G-G-R-I-D-R-I-G-A-NH$_2$

AP131    (desNH$_2$-F)-G-G-R-I-D-R-I-G-NH$_2$

\* AP132    (desNH$_2$-F)-G-G-R-I-D-R-I-NH$_2$

\* AP133    A-F-A$^\dagger$-G-R-I-D-R-I-G-A-NH$_2$

AP134    A-F-A$^\dagger$-G-R-I-D-R-I-G-NH$_2$

AP135    A-F-A$^\dagger$-G-R-I-D-R-I-NH$_2$

AP136    F-A$^\dagger$-G-R-I-D-R-I-G-A-NH$_2$

AP139  (desNH$_2$-F)-A†-G-R-I-D-R-I-G-A-NH$_2$

AP140  (desNH$_2$-F)-A†-G-R-I-D-R-I-G-NH$_2$

AP141  (desNH$_2$-F)-A†-G-R-I-D-R-I-NH$_2$

AP142  A-F-S†-G-R-I-D-R-I-G-A-NH$_2$

AP143  A-F-S†-G-R-I-D-R-I-G-NH$_2$

AP144  A-F-S†-G-R-I-D-R-I-NH$_2$

AP145  F-S†-G-R-I-D-R-I-G-A-NH$_2$

AP146  F-S†-G-R-I-D-R-I-G-NH$_2$

AP147  F-S†-G-R-I-D-R-I-NH$_2$

AP148  (desNH$_2$-F)-S†-G-R-I-D-R-I-G-A-NH$_2$

AP149  (desNH$_2$-F)-S†-G-R-I-D-R-I-G-NH$_2$

AP150  (desNH$_2$-F)-S†-G-R-I-D-R-I-NH$_2$

AP163    (desNH₂-F)-G-A†-R-I-D-R-I-G-A-NH₂

AP164    (desNH₂-F)-G-A†-R-I-D-R-I-G-NH₂

AP165    (desNH₂-F)-G-A†-R-I-D-R-I-NH₂

AP166    A-F-G-G-R-I-D-R-I-G-A₊-NH₂

AP167    F-G-G-R-I-D-R-I-G-A†-NH₂

AP168    (desNH₂-F)-G-G-R-I-D-R-I-G-A₊-NH₂

AP169    A-F-G-G-R-I-D-R-I-A†-A-NH₂

AP170    F-G-G-R-I-D-R-I-A₊-A-NH₂

AP171    (desNH₂-F)-G-G-R-I-D-R-I-A₊-A-NH₂

AP174 (desNH$_2$-F)-G-G-R-I-D-R-I-A†-NH$_2$

AP175 Y-A-F-G-G-R-I-D-R-I-G-A-NH$_2$

AP176 A-F-G-G-R-I-D-R-I-G-Y-NH$_2$

AP177 A-F-G-G-R-I-E-R-I-G-A-NH$_2$

AP178 A-F-G-G-K-I-E-R-I-G-A-NH$_2$

AP179 A-F-G-G-K-I-D-R-I-G-A-NH$_2$

AP180 A-F-G-G-R-I-D-K-I-G-A-NH$_2$

AP181 (desNH$_2$-F)-G-G-R-M-D-R-I-G-A-NH$_2$

AP182 (desNH$_2$-F)-G-G-R-M-D-R-I-G-NH$_2$

AP183 (desNH$_2$-F)-G-G-R-M-D-R-I-NH$_2$

AP190   (desNH$_2$-F)-A$^\dagger$-G-R-M-D-R-I-G-A-NH$_2$

AP191   (desNH$_2$-F)-A$^\dagger$-G-R-M-D-R-I-G-NH$_2$

AP192   (desNH$_2$-F)-A$^\dagger$-G-R-M-D-R-I-NH$_2$

AP193   A-F-S$^\dagger$-G-R-M-D-R-I-G-A-NH$_2$

AP194   A-F-S$^\dagger$-G-R-M-D-R-I-G-NH$_2$

AP195   A-F-S$^\dagger$-G-R-M-D-R-I-NH$_2$

AP196   F-S$^\dagger$-G-R-M-D-R-I-G-A-NH$_2$

AP197   F-S$^\dagger$-G-R-M-D-R-I-G-NH$_2$

AP198   F-S$^\dagger$-G-R-M-D-R-I-NH$_2$

AP199   (desNH$_2$-F)-S$^\dagger$-G-R-M-D-R-I-G-A-NH$_2$

AP200   (desNH$_2$-F)-S$^\dagger$-G-R-M-D-R-I-G-NH$_2$

AP201   (desNH$_2$-F)-S$^\dagger$-G-R-M-D-R-I-NH$_2$

AP202   A-F$^\dagger$-G-G-R-M-D-R-I-G-A-NH$_2$

AP203   A-F$^\dagger$-G-G-R-M-D-R-I-G-NH$_2$

AP204   A-F$^\dagger$-G-G-R-M-D-R-I-NH$_2$

AP205   F$^\dagger$-G-G-R-M-D-R-I-G-A-NH$_2$

AP206   F$^\dagger$-G-G-R-M-D-R-I-G-NH$_2$

AP207   F$^\dagger$-G-G-R-M-D-R-I-NH$_2$

AP214  (desNH$_2$-F)-G-A†-R-M-D-R-I-G-A-NH$_2$

AP215  (desNH$_2$-F)-G-A†-R-M-D-R-I-G-NH$_2$

AP216  (desNH$_2$-F)-G-A†-R-M-D-R-I-NH$_2$

AP217  A-F-G-G-R-M-D-R-I-G-A†-NH$_2$

AP218  F-G-G-R-M-D-R-I-G-A†-NH$_2$

AP219  (desNH$_2$-F)-G-G-R-M-D-R-I-G-A†-NH$_2$

AP220  A-F-G-G-R-M-D-R-I-A†-A-NH$_2$

AP221  F-G-G-R-M-D-R-I-A†-A-NH$_2$

AP222  (desNH$_2$-F)-G-G-R-M-D-R-I-A†-A-NH$_2$

AP223  A-F-G-G-R-M-D-R-I-A†-NH$_2$

AP224  F-G-G-R-M-D-R-I-A†-NH$_2$

AP225  (desNH$_2$-F)-G-G-R-M-D-R-I-A†-NH$_2$

\* AP302    A-F-G-G-R-I$^\dagger$-D-R-I-G-A-NH$_2$

\* AP304    A-F-G-G-R-I-D-R$^\dagger$-I-G-A-NH$_2$

\* AP305    A-F-G-G-R-I-D-R-I$^\dagger$-G-A-NH$_2$

Part B

\* AP306    (2-NA)-G-G-R-I-D-R-I-G-A-NH$_2$

\* AP307    (2-NOA)-NH(CH$_2$)$_4$CO-R-I-D-R-I-NH$_2$

\* AP308    (TPP)-G-G-R-I-D-R-I-NH$_2$

\* AP309    (1-AA)-G-G-R-I-D-R-I-NH$_2$

\* AP310    (CBZ)-G-G-R-I-D-R-I-NH$_2$

Fig. 4-7

* AP311 (FMOC)-G-G-R-I-D-R-I-NH$_2$

* AP312 (FMOC)-G-G-R-I-D-R-I-G-A-NH$_2$

* AP313 (IP)-G-G-R-I-D-R-I-G-A-NH$_2$

* AP314 (2-NA)-G-G-R-I-D-R-I-NH$_2$

* AP315 (1-NA)-G-G-R-I-D-R-I-G-A-NH$_2$

* AP316 (1-NOA)-G-G-R-I-D-R-I-NH$_2$

* AP317 (4-BPA)-G-G-R-I-D-R-I-NH$_2$

* AP318 (2-NOA)-G-G-R-I-D-R-I-G-A-NH$_2$

* AP319 (2-NOA)-G-G-R-I-D-R-I-NH$_2$

* AP320 (2-NA)-G-(Sar)-R-I-D-R-I-NH$_2$

* AP321 (2-NA)-G-(Aib)-R-I-D-R-I-NH$_2$

* AP322 (2-NOA)-A$^\dagger$-G-R-I-D-R-I-NH$_2$

* AP323 (FMOC)-NH(CH$_2$)$_4$CO-R-I-D-R-I-NH$_2$

* AP324 (2-NA)-NH(CH$_2$)$_4$CO-R-I-D-R-I-NH$_2$

* AP325 (2-NOA)-NH(CH$_2$)$_5$CO-R-I-D-R-I-NH$_2$

* AP326 (FMOC)-NH(CH$_2$)$_3$CO-R-I-D-R-I-NH$_2$

* AP327 (2-NA)-NH(CH$_2$)$_3$CO-R-I-D-R-I-NH$_2$

* AP328 (2-NA)-G-G-R-I-D-R-I-NHCH$_2$CH$_3$

* AP330   (2-NA)-S$^\dagger$-G-R-I-D-R-I-NH$_2$

* AP331   (3-DPP)-G-G-R-I-D-R-I-G-A-NH$_2$

* AP332   (2-NA)-G-G-R-I-D-R-L-NH$_2$

* AP333   (2-NA)-G-G-R-I-D-R-V-NH$_2$

* AP334   (CHA)-G-G-R-I-D-R-I-NH$_2$

AP335   (2-NOA)-G-G-R-M-D-Q-I-G-A-NH$_2$

AP336   (2-NOA)-G-G-R-M-D-Q-I-G-NH$_2$

* AP337   (2-NOA)-G-G-R-M-D-Q-I-NH$_2$

AP338   (2-NOA)-G-G-A-I-D-R-I-NH$_2$

AP339   (2-NOA)-G-G-A-I-D-R-I-G-NH$_2$

AP340   (2-NOA)-G-G-A-I-D-R-I-G-A-NH$_2$

AP341   (2-NOA)-G-G-A-M-D-R-I-G-A-NH$_2$

AP342   (2-NOA)-G-G-A-M-D-R-I-G-NH$_2$

AP343   (2-NOA)-G-G-A-M-D-R-I-NH$_2$

AP363    (2-NOA)-G-G-R-I-D-R-V-NH2

AP364    (2-NOA)-G-G-R-M-D-R-V-NH2
```

Fig. 4-10

* AP365   (2-NOA)-G-G-R-I-D-R-L-NH₂

AP366   (2-NOA)-G-G-R-I-D-R-M-NH₂

AP367   (2-NOA)-G-G-R-M-D-R-M-NH₂

AP368   (2-NOA)-G-G-R-M-D-R-L-NH₂

AP369   (2-NOA)-G-G-R-I-D-Q-I-NH₂

AP370   (2-NOA)-G-G-R-I-D-Q-I-G-NH₂

AP371   (2-NOA)-G-G-R-I-D-Q-I-G-A-NH₂

AP374   (2-NOA)-G-(Aib)-R-I-D-R-I-NH₂

AP375   (2-NOA)-G-(Aib)-R-I-D-R-I-G-NH₂

AP376   (2-NOA)-G-(Aib)-R-I-D-R-I-G-A-NH₂

AP377   (2-NOA)-G-(Aib)-R-M-D-R-I-G-A-NH₂

AP378   (2-NOA)-G-(Aib)-R-M-D-R-I-G-NH₂

AP379   (2-NOA)-G-(Aib)-R-M-D-R-I-NH₂

AP380   (2-NOA)-G-(Sar)-R-I-D-R-I-G-NH₂

AP381   (2-NOA)-G-(Sar)-R-I-D-R-I-NH₂

AP382   (2-NOA)-G-(Sar)-R-I-D-R-I-G-A-NH₂

AP383   (2-NOA)-G-(Sar)-R-M-D-R-I-G-A-NH₂

AP384   (2-NOA)-G-(Sar)-R-M-D-R-I-G-NH₂

Fig. 4-11

```
AP385    (2-NOA)-G-(Sar)-R-M-D-R-I-NH₂

AP386    (2-NA)-G-(Sar)-R-I-D-R-I-G-NH₂

AP387    (2-NA)-G-(Sar)-R-I-D-R-I-G-A-NH₂

AP388    (2-NA)-G-(Sar)-R-M-D-R-I-G-A-NH₂

AP389    (2-NA)-G-(Sar)-R-M-D-R-I-G-NH₂

* AP390  (2-NA)-G-(Sar)-R-M-D-R-I-NH₂

AP391    (2-NOA)-G-G-R-I-D-R-I-NHCH₂CH₃

AP393    (2-NOA)-G-G-R-I-D-R-I-G-NH₂

AP394    (2-NOA)-G-G-R-M-D-R-I-G-A-NH₂

AP395    (2-NOA)-G-G-R-M-D-R-I-G-NH₂

AP396    (2-NOA)-G-G-R-M-D-R-I-NH₂

AP397    (2-NOA)-S†-G-R-M-D-R-I-G-NH₂

AP398    (2-NOA)-S†-G-R-M-D-R-I-NH₂

AP399    (2-NOA)-G-A†-R-I-D-R-I-NH₂

AP400    (2-NOA)-G-A†-R-I-D-R-I-G-NH₂

AP401    (2-NOA)-G-A†-R-M-D-R-I-G-A-NH₂

AP402    (2-NOA)-G-A†-R-M-D-R-I-G-NH₂

AP403    (2-NOA)-G-A†-R-M-D-R-I-NH₂
```

AP410    (2-NA)-G-(Aib)-R-I-D-R-I-G-NH$_2$

AP411    (2-NA)-G-(Aib)-R-I-D-R-I-G-A-NH$_2$

AP412    (2-NA)-G-(Aib)-R-M-D-R-I-G-A-NH$_2$

AP413    (2-NA)-G-(Aib)-R-M-D-R-I-G-NH$_2$

* AP414    (2-NA)-G-(Aib)-R-M-D-R-I-NH$_2$

* AP415    (2-NOA)-NH(CH$_2$)$_3$CO-R-I-D-R-I-NH$_2$

AP416    (2-NOA)-NH(CH$_2$)$_3$CO-R-I-D-R-I-G-NH$_2$

AP417    (2-NOA)-NH(CH$_2$)$_3$CO-R-I-D-R-I-G-A-NH$_2$

AP418    (2-NOA)-NH(CH$_2$)$_3$CO-R-M-D-R-I-G-A-NH$_2$

AP419    (2-NOA)-NH(CH$_2$)$_3$CO-R-M-D-R-I-G-NH$_2$

AP420    (2-NOA)-NH(CH$_2$)$_3$CO-R-M-D-R-I-NH$_2$

AP421    (2-NOA)-NH(CH$_2$)$_5$CO-R-I-D-R-I-G-NH$_2$

Fig. 4-13

```
AP422    (2-NOA)-NH(CH₂)₅CO-R-I-D-R-I-G-A-NH₂

AP423    (2-NOA)-NH(CH₂)₅CO-R-M-D-R-I-G-A-NH₂

AP424    (2-NOA)-NH(CH₂)₅CO-R-M-D-R-I-G-NH₂

AP425    (2-NOA)-NH(CH₂)₅CO-R-M-D-R-I-NH₂

AP426    (2-NA)-NH(CH₂)₅CO-R-M-D-R-I-NH₂

AP427    (2-NA)-NH(CH₂)₅CO-R-M-D-R-I-G-NH₂

AP428    (2-NA)-NH(CH₂)₅CO-R-M-D-R-I-G-A-NH₂

* AP429  (2-NA)-NH(CH₂)₅CO-R-I-D-R-I-G-A-NH₂

AP430    (2-NA)-NH(CH₂)₅CO-R-I-D-R-I-G-NH₂

AP431    (2-NA)-S†-G-R-I-D-R-I-G-NH₂

AP432    (2-NA)-S†-G-R-I-D-R-I-G-A-NH₂

AP433    (2-NA)-S†-G-R-M-D-R-I-G-A-NH₂

AP434    (2-NA)-S†-G-R-M-D-R-I-G-NH₂

AP435    (2-NA)-S†-G-R-M-D-R-I-NH₂

AP436    (2-NOA)-S†-G-R-I-D-R-I-NH₂

AP437    (2-NOA)-S†-G-R-I-D-R-I-G-NH₂

AP438    (2-NOA)-S†-G-R-I-D-R-I-G-A-NH₂

AP439    (2-NOA)-S†-G-R-M-D-R-I-G-A-NH₂
```

AP446   (2-NOA)-A†-G-R-I-D-R-I-G-NH$_2$

AP447   (2-NOA)-A†-G-R-I-D-R-I-G-A-NH$_2$

AP448   (2-NOA)-A†-G-R-M-D-R-I-G-A-NH$_2$

AP449   (2-NOA)-A†-G-R-M-D-R-I-G-NH$_2$

AP450   (2-NOA)-A†-G-R-M-D-R-I-NH$_2$

AP451   (2-NA)-NH(CH$_2$)$_3$CO-R-I-D-R-I-G-NH$_2$

AP452   (2-NA)-NH(CH$_2$)$_3$CO-R-I-D-R-I-G-A-NH$_2$

AP453   (2-NA)-NH(CH$_2$)$_3$CO-R-M-D-R-I-G-A-NH$_2$

AP454   (2-NA)-NH(CH$_2$)$_3$CO-R-M-D-R-I-G-NH$_2$

AP455   (2-NA)-NH(CH$_2$)$_3$CO-R-M-D-R-I-NH$_2$

AP456   (2-NOA)-NH(CH$_2$)$_4$CO-R-I-D-R-I-G-NH$_2$

AP457   (2-NOA)-NH(CH$_2$)$_4$CO-R-I-D-R-I-G-A-NH$_2$

Fig. 4-15

AP458   (2-NOA)-NH(CH$_2$)$_4$CO-R-M-D-R-I-G-NH$_2$

* AP459   (2-NOA)-NH(CH$_2$)$_4$CO-R-M-D-R-I-NH$_2$

AP460   (2-NOA)-NH(CH$_2$)$_4$CO-R-I-D-R-V-NH$_2$

AP461   (2-NOA)-NH(CH$_2$)$_4$CO-R-I-D-R-L-NH$_2$

AP462   (2-NOA)-NH(CH$_2$)$_4$CO-R-I-D-R-M-NH$_2$

AP463   (2-NOA)-NH(CH$_2$)$_4$CO-R-M-D-R-M-NH$_2$

AP464   (2-NOA)-NH(CH$_2$)$_4$CO-R-M-D-R-V-NH$_2$

AP465   (2-NOA)-NH(CH$_2$)$_4$CO-R-M-D-R-L-NH$_2$

AP466   (2-NOA)-NH(CH$_2$)$_4$CO-R-L-D-R-L-NH$_2$

AP467   (2-NOA)-NH(CH$_2$)$_4$CO-R-L-D-R-M-NH$_2$

AP468   (2-NOA)-NH(CH$_2$)$_4$CO-R-L-D-R-V-NH$_2$

AP469   (2-NOA)-NH(CH$_2$)$_4$CO-R-L-D-R-I-NH$_2$

AP470   (2-NOA)-NH(CH$_2$)$_4$CO-R-V-D-R-I-NH$_2$

AP471   (2-NOA)-NH(CH$_2$)$_4$CO-R-V-D-R-V-NH$_2$

AP472   (2-NOA)-NH(CH$_2$)$_4$CO-R-V-D-R-L-NH$_2$

AP473   (2-NOA)-NH(CH$_2$)$_4$CO-R-V-D-R-M-NH$_2$

AP474   (2-NOA)-NH(CH$_2$)$_4$CO-A-I-D-R-I-NH$_2$

AP475   (2-NOA)-NH(CH$_2$)$_4$CO-A-M-D-R-I-NH$_2$

Fig. 4-16

AP476 (2-NOA)-NH(CH$_2$)$_4$CO-R-I-D-Q-I-NH$_2$

AP477 (2-NOA)-NH(CH$_2$)$_4$CO-R-I-D-Q-I-G-NH$_2$

AP478 (2-NOA)-NH(CH$_2$)$_4$CO-R-I-D-Q-I-G-A-NH$_2$

AP479 (2-NOA)-NH(CH$_2$)$_4$CO-R-M-D-Q-I-G-A-NH$_2$

AP480 (2-NOA)-NH(CH$_2$)$_4$CO-R-M-D-Q-I-G-NH$_2$

AP481 (2-NOA)-NH(CH$_2$)$_4$CO-R-M-D-Q-I-NH$_2$

AP509    (2-NOA)-G-G-R-I-D-R-NH-CH$_2$-CH(CH$_3$)$_2$

\* AP524   (2-NA)-G-G-R-I-D-R-I-G-NH-(ethyl)

\* AP525   (2-NA)-G-G-R-I-D-R-I-G-(Aib)-NH₂

\* AP526   (2-NA)-G-G-R-I-D-R-I-(5-aminovaleryl)-NH₂

\* AP527   (2-NA)-G-G-R-(Cha)-D-R-I-NH₂

\* AP528   2-(2'-(6'-MeONAP))-G-G-R-I-D-R-I-G-A-NH₂

\* AP529   (2-NA)-G-G-R-I-D-R-(N-MeIle)-G-NH-(ethyl)

\* AP530   (2-NA)-NH(CH₂)₄CO-R-I-D-R-I-G-NH-(ethyl)

\* AP531   (3-IB)-G-R-I-D-R-I-G-A-NH₂)

\* AP532   (3-IB)-beta-Ala-R-I-D-R-I-G-A-NH₂

\* AP533   (bis-(1'-NM)acetyl)-G-G-R-I-D-R-I-G-A-NH₂

\* AP534   (DBA)-G-G-R-I-D-R-I-G-A-NH₂

\* AP535   (2-NA)-G-G-R-I-D-R-V†-NH₂

\* AP536   (2-NA)-G-G-R-I-D-R-L†-NH₂

\* AP538   (2-NA)-

Fig. 4-19

* AP539 (2-NOA)-N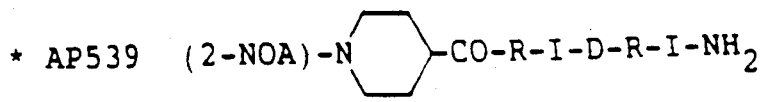CO-R-I-D-R-I-NH₂

* AP557 (2-NA)-N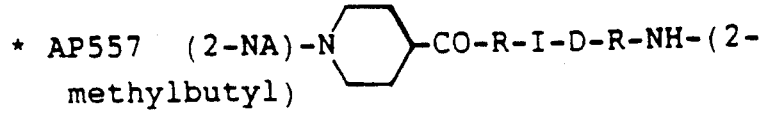CO-R-I-D-R-NH-(2-methylbutyl)

* AP560 (2-NA)-NH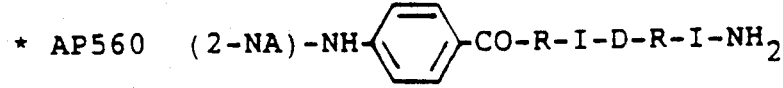CO-R-I-D-R-I-NH₂

AP561 (2-NTA)-NCO-R-I-D-R-I-NH₂

* AP562 (2-NYL)-NCO-R-I-D-R-I-NH₂

AP563 (3-POP)-NCO-R-I-D-R-I-NH₂

* AP564 (2-NA)-NH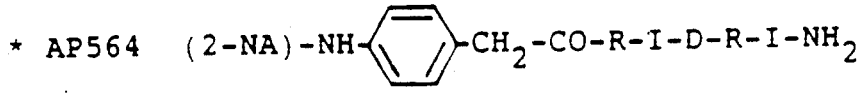CH₂-CO-R-I-D-R-I-NH₂

AP565 (2-NA)-NH-CH₂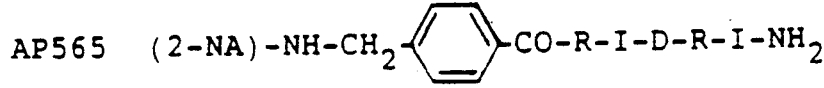CO-R-I-D-R-I-NH₂

AP566 (2-NA)-NH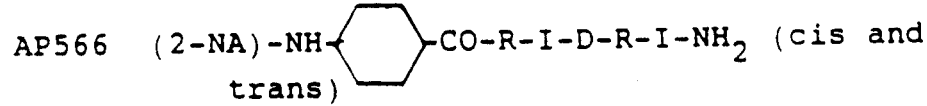CO-R-I-D-R-I-NH₂ (cis and trans)

AP567 (2-NOA)-NH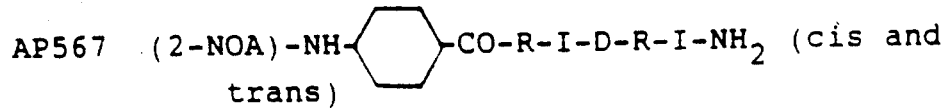CO-R-I-D-R-I-NH₂ (cis and trans)

* AP568 (2-NA)-NH-CH₂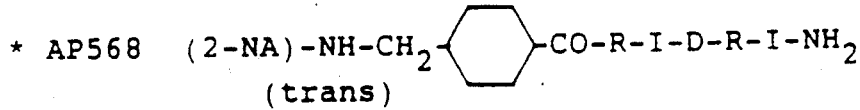CO-R-I-D-R-I-NH₂
    (trans)

AP569 (2-NOA)-NH-CH₂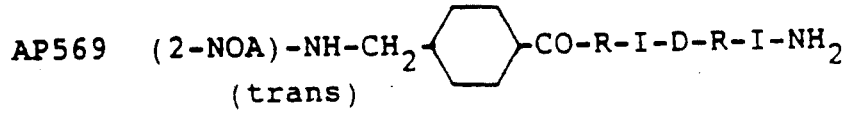CO-R-I-D-R-I-NH₂
    (trans)

AP570 (2-NL)-CH₂-CH₂-N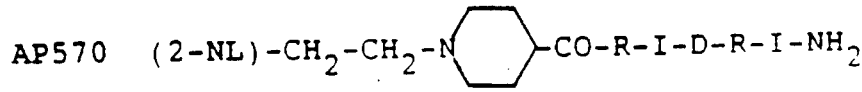CO-R-I-D-R-I-NH₂

AP571 (2-NO)-CH₂CH₂-N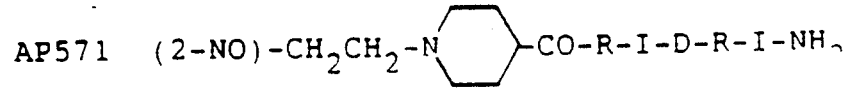CO-R-I-D-R-I-NH₂

AP572 (2-NYL)-NH-CH₂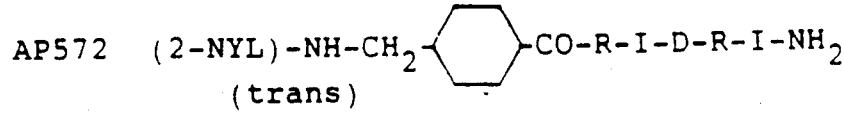CO-R-I-D-R-I-NH₂
    (trans)

Fig. 4-20

AP573 (2-NL)-CH₂-NH-CH₂-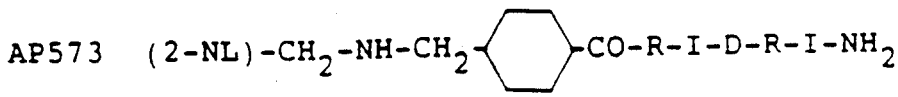-CO-R-I-D-R-I-NH₂

* AP574 (2-NYL)-CH₂-N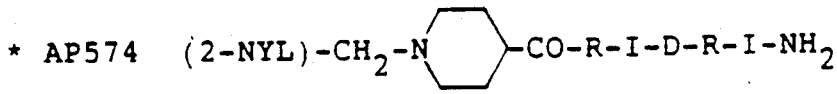-CO-R-I-D-R-I-NH₂

* AP576 (2-NOA)-NH(CH₂)₃CO-R-I-D-R-I-G-A-NH₂

* AP590 (2-NA)-G-G-R-tBuA-D-R-I-NH₂

* AP591 (2-NA)-G-G-R-tBuG-D-R-I-NH₂

* AP592 (2-NA)-G-G-R-I-D-Orn-I-NH₂

* AP593 (2-NA)-G-G-R-I-D-Cit-I-NH₂

* AP594 (2-NA)-G-G-R-I-D-R-tBuA-NH₂

* AP596 (2-NA)-G-G-R-I-D-R-NMeIle-NH(ethyl)

* AP597 (3-1B)-G-R-I-D-R-I-G-A-NH₂

AP598 (3-1B)-βala-R-I-D-R-I-G-A-NH₂

* AP599 (2-NA)-G-G-R-Cha-D-R-I-NH₂

AP700 2-NA-NH-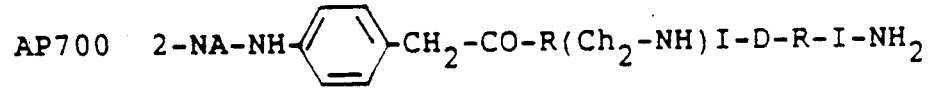-CH₂-CO-R(Ch₂-NH)I-D-R-I-NH₂

AP701 2-NA-NH-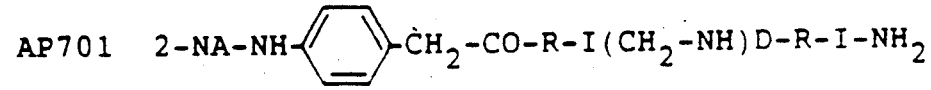-CH₂-CO-R-I(CH₂-NH)D-R-I-NH₂

AP702 2-NA-NH-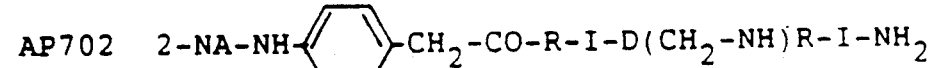-CH₂-CO-R-I-D(CH₂-NH)R-I-NH₂

AP703 2-NA-NH-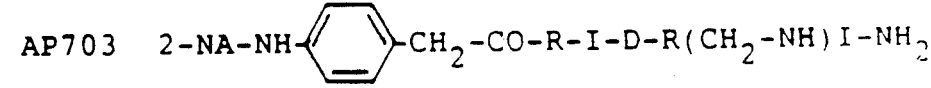-CH₂-CO-R-I-D-R(CH₂-NH)I-NH₂

* AP704 2-NA-N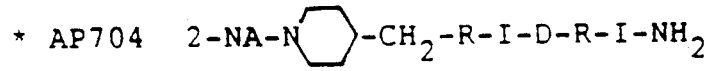-CH₂-R-I-D-R-I-NH₂

AP709    (TPP)-G-G-R-I-D-R-I-G-NH2

AP710    (TPP)-G-G-R-I-D-R-I-G-A-NH2

AP711    (TPP)-G-G-R-M-D-R-I-NH2

AP712    (TPP)-G-G-R-M-D-R-I-G-NH2

AP713    (TPP)-G-G-R-M-D-R-I-G-A-NH2

AP714    (1-AA)-G-G-R-I-D-R-I-G-NH2

AP715    (1-AA)-G-G-R-I-D-R-I-G-A-NH2

AP716    (1-AA)-G-G-R-M-D-R-I-NH2

AP717    (1-AA)-G-G-R-M-D-R-I-G-NH2

AP718    (1-AA)-G-G-R-M-D-R-I-G-A-NH2

AP719    (CBZ)-G-G-R-I-D-R-I-G-NH2

AP720    (CBZ)-G-G-R-I-D-R-I-G-A-NH2

AP721    (CBZ)-G-G-R-M-D-R-I-NH2

AP722    (CBZ)-G-G-R-M-D-R-I-G-NH2

AP723    (CBZ)-G-G-R-M-D-R-I-G-A-NH2
```

Fig. 4-22

AP724    (FMOC)-G-G-R-I-D-R-I-G-$NH_2$

AP725    (FMOC)-G-G-R-M-D-R-I-$NH_2$

AP726    (FMOC)-G-G-R-M-D-R-I-G-$NH_2$

AP727    (FMOC)-G-G-R-M-D-R-I-G-A-$NH_2$

AP728    (IP)-G-G-R-I-D-R-I-G-$NH_2$

AP729    (IP)-G-G-R-I-D-R-I-G-A-$NH_2$

AP730    (IP)-G-G-R-M-D-R-I-$NH_2$

AP731    (IP)-G-G-R-M-D-R-I-G-$NH_2$

AP732    (IP)-G-G-R-M-D-R-I-G-A-$NH_2$

AP733    (1-NA)-G-G-R-I-D-R-I-$NH_2$

AP734    (1-NA)-G-G-R-I-D-R-I-G-$NH_2$

AP735    (1-NA)-G-G-R-M-D-R-I-$NH_2$

AP736    (1-NA)-G-G-R-M-D-R-I-G-$NH_2$

AP737    (1-NA)-G-G-R-M-D-R-I-G-A-$NH_2$

AP738    (1-NOA)-G-G-R-I-D-R-I-G-$NH_2$

AP739    (1-NOA)-G-G-R-I-D-R-I-G-A-$NH_2$

AP740    (1-NOA)-G-G-R-M-D-R-I-$NH_2$

AP741    (1-NOA)-G-G-R-M-D-R-I-G-$NH_2$

Fig. 4-23

AP741    (1-NOA)-G-G-R-M-D-R-I-G-A-NH$_2$

AP734    (4-BPA)-G-G-R-I-D-R-I-G-NH$_2$

AP744    (4-BPA)-G-G-R-I-D-R-I-G-A-NH$_2$

AP745    (4-BPA)-G-G-R-M-D-R-I-NH$_2$

AP746    (4-BPA)-G-G-R-M-D-R-I-G-NH$_2$

AP747    (4-BPA)-G-G-R-M-D-R-I-G-A-NH$_2$

AP748    (FMOC)-NH(CH$_2$)$_4$CO-R-I-D-R-I-G-NH$_2$

AP749    (FMOC)-NH(CH$_2$)$_4$CO-R-I-D-R-I-G-A-NH$_2$

AP750    (FMOC)-NH(CH$_2$)$_4$CO-R-M-D-R-I-NH$_2$

AP751    (FMOC)-NH(CH$_2$)$_4$CO-R-M-D-R-I-G-NH$_2$

AP752    (FMOC)-NH(CH$_2$)$_4$CO-R-M-D-R-I-G-A-NH$_2$

AP753    (3-DPP)-NH(CH$_2$)$_3$CO-R-I-D-R-I-G-NH$_2$

AP754    (3-DPP)-NH(CH$_2$)$_3$CO-R-I-D-R-I-G-A-NH$_2$

AP755    (3-DPP)-NH(CH$_2$)$_3$CO-R-M-D-R-I-NH$_2$

AP756    (3-DPP)-NH(CH$_2$)$_3$CO-R-M-D-R-I-G-NH$_2$

AP757    (3-DPP)-NH(CH$_2$)$_3$CO-R-M-D-R-I-G-A-NH$_2$

AP758    (CHA)-G-G-R-I-D-R-I-G-NH$_2$

AP759    (CHA)-G-G-R-I-D-R-I-G-A-NH$_2$

Fig. 4-24

AP760    (CHA)-G-G-R-M-D-R-I-NH$_2$

AP761    (CHA)-G-G-R-M-D-R-I-G-NH$_2$

AP762    (CHA)-G-G-R-M-D-R-I-G-A-NH$_2$

AP763    (2-NA)-G-G-L-M-D-R-I-NH$_2$

AP764    (2-NA)-G-G-L-M-D-R-L-NH$_2$

AP765    (2-NA)-G-G-L-M-D-R-M-NH$_2$

AP766    (2-NA)-G-G-L-M-D-R-V-NH$_2$

AP767    (2-NA)-G-G-I-M-D-R-M-NH$_2$

AP768    (2-NOA)-G-G-L-M-D-R-I-NH$_2$

AP769    (2-NOA)-G-G-L-M-D-R-L-NH$_2$

AP770    (2-NOA)-G-G-L-M-D-R-M-NH$_2$

AP771    (2-NOA)-G-G-L-M-D-R-V-NH$_2$

AP772    (2-NOA)-G-G-I-V-D-R-M-NH$_2$

AP773    (2-NOA)-G-G-I-V-D-R-I-NH$_2$

AP774    (2-NOA)-G-G-I-V-D-R-L-NH$_2$

AP775    (2-NOA)-G-G-I-V-D-R-V-NH$_2$

AP776    (2-NOA)-G-A↑-R-I-D-R-I-G-A-NH$_2$

AP777    (2-NOA)-NH(CH$_2$)$_4$CO-R-M-D-R-I-G-A-NH$_2$

Fig. 4-25

AP778  (2-NOA)-NH(CH$_2$)$_4$CO-A-I-D-R-I-NH$_2$

AP779  (2-NOA)-NH(CH$_2$)$_4$CO-A-I-D-R-I-G-NH$_2$

AP780  (2-NOA)-NH(CH$_2$)$_4$CO-A-I-D-R-I-G-A-NH$_2$

AP781  (2-NOA)-NH(CH$_2$)$_4$CO-A-M-D-R-I-NH$_2$

AP782  (2-NOA)-NH(CH$_2$)$_4$CO-A-M-D-R-I-G-NH$_2$

AP783  (2-NOA)-NH(CH$_2$)$_4$CO-A-M-D-R-I-G-A-NH$_2$

AP784  (2-NOA)-G-G-R-I-D-R-NH-CH$_2$-CH(CH$_3$)CH$_2$CH$_3$

AP785  (2-NOA)-G-G-R-M-D-R-NH-CH$_2$-CH(CH$_3$)CH$_2$CH$_3$

AP786  (2-NA)-G-G-R-M-D-R-NH-CH$_2$-CH(CH$_3$)CH$_2$CH$_3$

AP787  (2-NOA)-G-G-R-M-D-R-NH-CH$_2$-CH(CH$_3$)$_2$

AP788  (2-NA)-G-G-R-M-D-R-NH-CH$_2$-CH(CH$_3$)$_2$

*AP789  (2-NOA)-NH-(CH$_2$)$_7$-CO-R-I-D-R-I-NH$_2$

*AP790  (2-NYL)-NH—⬡— CH$_2$-CO-R-I-D-R-I-NH$_2$

*AP791  (2-NOA)-NH—⬡— CO-R-I-D-R-I-NH$_2$

*AP792  (2-NOA)-NH—⬡— CH$_2$-CO-R-I-D-R-I-NH$_2$

*AP793  (2-NOA)-N⬡— CO-R-I-D-R-I-NH$_2$

*AP794  (2-NYL)-CH$_2$NH—⬡— CO-R-I-D-R-I-NH$_2$

*AP795  (2-NYL)-NHCH$_2$—⬡— CO-R-I-D-R-I-NH$_2$

AP797  (2-NYL)-NH—⟨◯⟩—CH₂-CO-R-M-D-R-I-NH₂

*AP798  (2-NOA)-NH—⟨◯⟩—CH₂-CO-K-I-D-R-I-NH₂

*AP799  (2-NA)-NH—⟨◯⟩—CH₂CO-R-I-D-K-I-NH₂

*AP800  (2-NA)-NH—⟨◯⟩—CH₂-CO-K-I-D-R-I-NH₂

*AP801  (2-NOA)-NH—⟨◯⟩—CH₂-CO-(Acetyl)Lys-I-D-R-I-NH₂

*AP802  (2-NYL)-NH—⟨◯⟩—CH₂-CO-K-I-D-R-I-NH₂

AP803  (2-NYL)-NH—⟨◯⟩—CH₂-CO-R-I-D-K-I-NH₂

AP804  (2-NYL)-NH—⟨◯⟩—CH₂-CO-R-I-D-R-[D-Ile]-NH₂

AP805  (2-NYL)-NH—⟨◯⟩—CH₂-CO-R-L-D-R-I-NH₂

*AP806  (2-NA)-NH—⟨◯⟩—CH₂CO-K(CH₂NH)I-D-R-I-NH₂

*AP807  (2-NA)-NH—⟨◯⟩—CH₂-CO-R-I-D-K(CH₂NH)I-NH₂

*AP808  (2-NOA)-NH—⟨◯⟩—CH₂CO-K(CH₂NH)I-D-R-I-NH₂

*AP809  (2-NYL)-NH—⟨◯⟩—CH₂-CO-K(CH₂NH)I-D-R-I-NH₂

*AP810  (2-NOA)-N⟨◯⟩—CO-R-I-D-R-NH-(S)-2-methylbutyl

*AP811  (2-NYL)-NH—⟨◯⟩—CH₂CO-R-I-D-R-NH-(S)-2-methylbutyl

Fig.4-27

* AP812 (2-NOA)-N-CH$_2$NH-R-I-D-R-NH-(S)-2-methylbutyl
* AP813 (2-NOA)-NH--CH$_2$CO-R-I-D-R-NH-(S)-2-methylbutyl
* AP814 (2-NYL)-NH--CH$_2$-CO-K(CH$_2$NH)I-D-R-NHCH$_2$CH(CH$_3$)CH$_2$CH$_3$
AP815 (2-NOA)-NH--CH$_2$CO-Orn-I-D-R-I-NH$_2$
AP816 (2-NOA)-NH--CH$_2$(CH$_2$NH)R-I-D-R-I-NH$_2$
AP817 (2-ClPA)-NH--CH$_2$CO-R-I-D-R-I-NH$_2$
AP818 (2-BrPA)-NH--CH$_2$CO-R-I-D-R-I-NH$_2$
AP819 (2-BrAF)-NH--CH$_2$CO-R-I-D-R-I-NH$_2$
Fig. 4-28

* AP105   G-G-R-I-D-R-I-G-A-A-NH$_2$

* AP106   G-R-I-D-R-I-G-A-A-NH$_2$

* AP107   R-I-D-R-I-G-A-A-NH$_2$

* AP120   Acetyl-G-G-R-I-D-R-I-NH$_2$

AP121   G-R-I-D-R-I-NH$_2$

AP123   G-G-R-I-D-R-I-G-NH$_2$

AP124   G-R-I-D-R-I-G-NH$_2$

AP125   R-I-D-R-I-G-NH$_2$

AP127   G-G-R-I-D-R-I-G-A-NH$_2$

AP128   G-R-I-D-R-I-G-A-NH$_2$

AP129   R-I-D-R-I-G-A-NH$_2$

AP291   Acetyl-G-G-R-M-D-R-I-NH$_2$

\* AP301    A-F-G-G-R$^\dagger$-I-D-R-I-G-A-NH$_2$

\* AP303    A-F-G-G-R-I-D$^\dagger$-R-I-G-A-NH$_2$

AP512    (2-NA)-G-G-L-I-D-R-I-NH$_2$

AP514    (2-NA)-G-G-Nle-I-D-R-I-NH$_2$

AP515    (2-NA)-G-G-R-MSO-D-R-I-NH$_2$

AP516    (2-NA)-G-G-R-I-D-S-I-NH$_2$

AP519    (2-NA)-G-G-R-I-D-R-P-NH$_2$

AP521    (2-NA)-G-G-R-F-D-R-I-NH$_2$

AP537    (2-NA)-G-G-R-I-D-R-F$^\dagger$-NH$_2$

AP558    (2-NA)-G-G-R-I-(beta-Asp$^\dagger$)-R-I-NH$_2$

AP559    (2-NA)-G-G-R-I-(beta-Asp)-R-I-NH$_2$

AP575    (2-NA)-G-G-R-Phg-D-R-I-NH$_2$

AP595    (2-NA)-G-G-R-I-D-R-Phg-NH$_2$

Fig. 5-2

LINEAR ANALOGS OF ATRIAL NATRIURETIC PEPTIDES

This application is a continuation-in-part of U.S. Ser. No. 237,299 filed Aug. 26, 1988 and now abandoned, which is a continuation-in-part of U.S. Ser. No. 138,893 filed Dec. 24, 1987 and now abandoned, which is a continuation-in-part of U.S. Ser. No. 921,360 filed Oct. 28, 1986 and now abandoned, which is a continuation-in-part of U.S. Ser. No. 904,091 filed Sept. 4, 1986 and now abandoned, which is a continuation-in-part of U.S. Ser. No. 868,312 filed May 28, 1986 and now issued as U.S. Pat. No. 4,757,048, which is a continuation-in-part of U.S. Ser. No. 795,220 filed Nov. 5, 1985 and now abandoned. U.S. Ser. No. 168,661 filed Mar. 16, 1988 is a continuation of U.S. Ser. No. 921,360 and therefore also a continuation-in-part of the applications listed above that were filed prior thereto and has now issued as U.S. Pat. No. 4,804,650.

DESCRIPTION

1. Technical Field

The present invention relates generally to synthetic analogs of atrial peptides and more particularly to synthetic linear peptide compounds which find use as diuretics, natriuretics and/or vasodilators, or as intermediates for or modulators of such useful compounds, together with methods for their production and use.

2. Background Art

Most multi-cellular organisms are organized into tissues and organs which perform specialized functions. Thus, a system has evolved to transport and circulate materials between them. In higher animals, including mammals, this circulatory system is closed, in order to improve the efficiency of transport. The flow of blood fluid through this closed cardiovascular system requires that the fluid be maintained under pressure and the regulation of the systemic arterial blood pressure requires a complex interaction of numerous factors including, e.g., fluid volume and vascular elasticity and caliber.

The maintenance of normal extracellular fluid volume depends primarily on the excretion of sodium (natriuresis) and water (diuresis) by the kidneys. This is determined by (1) the rate at which plasma is filtered at the glomerulus (glomerular filtration rate, or GFR) and (2) the degree to which sodium is actively reabsorbed along the renal tubule (with water following passively). The latter process is in part regulated by the adrenal steroid hormone aldosterone. It has been long believed that, in addition to GFR and aldosterone, there must be a "third factor" which also regulates sodium reabsorption. It is now apparent that many of the phenomena which required the postulation of a "third factor" can be explained by the effects of physical forces (e.g., blood pressure, red blood cell concentration and plasma viscosity) on sodium reabsorption. Nonetheless, the search continues for a "natriuretic hormone" which might modulate tubular reabsorption.

A natriuretic effect has been demonstrated by crude extracts of rat atrial tissue but not ventricular tissue. De Bold, A. J., et al., Life Sciences, 28:89–94 (1981), Garcia, R., Experientia, 38:1071–73 (1982), Currie, M. G., et al., Science 221:71–73 (1983). Various peptides with diuretic and natriuretic properties have been isolated from atrial tissue and sequenced. Flynn, T. G., et al., Biochem. Biophys. Res. Commun. 117:859–865f (1983), Currie, M. G., et al., Science 223:67–69 (1984), Kangawa, K., et al., Biochem. Biophys. Res. Commun. 118:131–139 (1984).

More recently, various seemingly related peptides have been isolated, sequenced and shown to have natriuretic, diuretic and vasorelaxant activity in varying degrees. U.S. Patent No. 4,496,544: U.S. Pat. No. 4,508,712; Kangawa, K., et al., Biochem. Biophys. Res. Commun. 121(2):585–591 (1984); Kangawa, K., et al., Biochem. Biophys. Res. Commun. 119(3):933–940; Garcia, R., et al., Biochem. Biophys. Res. Commun. 126(1):178–184 (1985); Katsube, N., et al., Biochem. Biophys. Res. Commun. 128(1):325–330 (1985).

The existence of these atrial natriuretic factors strengthens the long-held suspicion that the heart, aside from its obvious influence on renal perfusion, plays an important role in regulating renal sodium and water excretion.

A number of clinically important disease states are characterized by abnormal fluid volume retention. Congestive heart failure, cirrhosis of the liver and the nephrotic syndrome each lead to excessive fluid accumulation on the venous side of the circulation, the presumed common mechanism being under-perfusion of the kidneys leading to a fall in GFR. In addition, the reduced renal perfusion stimulates excessive secretion of renin, a proteolytic enzyme whose action in the circulation leads to the formation of angiotensin. Angiotensin is a powerful constrictor of arterioles (which helps to maintain arterial pressure) and also stimulates release of the sodium-retaining hormone aldosterone by the adrenal gland (which further worsens fluid retention). These mechanisms do not, however, fully account for the fluid retention of the so-called "edematous states," and additional factors are likely to be involved.

An increase in extracellular fluid volume is also thought to contribute to the development of hypertension in many instances. Hypertension, or chronically elevated blood pressure, is one of the major causes of illness and death worldwide. It is estimated that more than 20 million Americans suffer from this disease whose complications include heart failure, heart attack, stroke and kidney failure. The major observed hemodynamic abnormality in chronic hypertension is increased resistance to the flow of blood through the arterioles. The mechanisms which lead to this increased "peripheral resistance" are, however, incompletely understood. In some cases inappropriate activity of the renin-angiotensin system or sympathetic nervous system may lead to excessive constriction of the arterioles; by "inappropriate" it is meant that the unknown signal(s) leading to this activity are not based upon a physiological need of the organism, and thus lead to elevated blood pressure. In a substantial fraction of hypertensives, however, inappropriate sodium and volume retention by the kidney is felt to either initiate or contribute to the elevated blood pressure. The responsible defect in kidney function and the mechanism whereby fluid retention leads to increased peripheral resistance are both unknown. It is possible that a relative deficiency of a natriuretic hormone could be responsible for these observations, particularly if the same substance also normally exerted a relaxant effect on arterioles.

Diuretic therapy is currently a mainstay in the treatment of hypertension, renal failure and the various edematous states (heart failure, etc.). Currently available pharmacological preparations have, however, several important limitations and undesirable effects. While their use may be directed at a specific abnormality (i.e., volume expansion), their multiple actions are undoubtedly not physiological, leading for instance to potassium depletion, increased retention of uric acid and abnormal glucose and lipid metabolism. In addition, all known diuretics profoundly stimulate the renin-angiotensinaldosterone system, which counteracts their volume-depleting and blood pressure-lowering effects and leads to other unwanted effects. It would be desirable to provide a pharmacologically effective compound which can regulate blood pressure by providing a complete but controlled range of physiological responses.

However, the isolation of such compounds from atrial tissue is typically a cumbersome process and requires substantial substrate tissue to produce minute quantities of the compounds.

Furthermore, it is considered desirable to provide modifications to the native structures reported for these atrial natriuretic factors in order to isolate the regions of the peptides responsible for the distinct biological activities or regions important in the metabolism and clearance of the peptide. Having determined the appropriate units of activity, structural analogs can be created which preserve, e.g., natriuretic or diuretic activity. Furthermore, shortened peptide sequences will provide active synthetic analogs which can be taken orally or delivered intranasally to provide the therapeutic benefits of the native compositions.

Shortened and modified peptide sequences will also desirably be formulated to enhance their direct or indirect biological activity, resistance to degradation, biological half-life and to enable the chemosynthetic production of these compounds in a cost-effective manner for clinical use.

DISCLOSURE OF THE INVENTION

It has now been found that a class of linear synthetic analogs of native Atrial Natriuretic Peptides (ANPs) which have been prepared in accordance with the present invention is capable of exhibiting or modulating the natriuretic, diuretic and/or vasorelaxant activity of the endogenous or native peptides in mammals in vivo. The native peptides are cyclic by virtue of a cystine disulfide bridge; the compounds of the invention are not cyclic.

Most of the synthetic analog compounds of the present invention retain a core pentapeptide sequence of amino acid residues which correspond in a defined way to the sequence $A_8$–$AA_{12}$ of native ANPs, using the identification system from Atlas, S., et al., Nature 309:717-719 (1984) wherein the amino-terminal arginine residue is at position 1. In the known native ANPs, this core sequence is RIDRI in rat and RMDRI in human. Certain defined permutations of this sequence, including some wherein $AA_{12}$ is not present, retain activity in vivo and demonstrate that the core peptide structure is a significant factor in the peptides, biological activity. However, as explained hereinbelow, many of these compounds are not active in in vitro model systems for assay of diuretic or natriuretic activities. It is likely that these analogs empower the function of endogenous ANPs by blocking clearance receptor(s) for these peptides.

The present invention is, therefore, in one aspect directed to linear analog peptide compounds having natriuretic, diuretic and/or vasorelaxant activity in mammals which have the formula:

$$Z_1Z_2\text{-}AA_8\text{-}AA_9\text{-}AA_{10}\text{-}AA_{11}\text{-}AA_{12}\text{-}Z_3 \qquad (1)$$

ps wherein:

each of $AA_8$ and $AA_{11}$ is, independently, preferably a basic/noncyclic, but can be also a neutral/nonpolar/small or neutral/polar/large/nonaromatic amino acid residue; in addition, $AA_8$ can be a neutral/nonpolar/large/nonaromatic amino acid;

$AA_9$ is a neutral/nonpolar/large/nonaromatic amino acid residue in the D or L configuration;

$AA_{10}$ is an acidic amino acid residue; and $AA_{12}$ is a neutral/nonpolar/large/nonaromatic amino acid residue, in the D or L configuration or is a covalent bond;

wherein $Z_1$ is a peptide of from 1 to 125 amino acids having as its carboxy-terminal residue a hydrophobic amino acid residue, or the desNH$_2$ form thereof, or is a hydrophobic aliphatic, aromatic, or mixed aliphatic/aromatic organic group of from 6 to 20 carbon atoms, $Z_2$ is a spacer group which provides a spaced dimension of about 4.5-15 angstroms, i.e., contains 3-9 atoms in a linked group or can be conformed to the proper spacing by folding; and $Z_3$ is (OH), NH$_2$, NHR' or NR'R'' wherein R' or R'' are each independently straight or branched chain alkyl of 1-10 carbon atoms wherein 1 or 2 carbons may be replaced by O, N, or S, or $Z_3$ is a peptide residue of 1-20 amino acid residues, or an amide or alkyl amide thereof, with the proviso that when $AA_{12}$ is a covalent bond, $Z_3$ cannot be OH, NH$_2$ or a peptide.

In the foregoing compounds of the invention, one or more of the amide backbone linkages between any adjacent amino acid residues may optionally be replaced by a linkage selected from the group consisting of —CH$_2$NH—, —CH$_2$—S—, —CH$_2$CH$_2$—, —CH=CH— (cis and trans), —COCH$_2$—, —CH(OH)CH$_2$ and —CH$_2$SO—.

One or two of the residues in the peptides of the invention may be replaced by the corresponding D isomer, in addition to, or instead of, $AA_9$ and $AA_{12}$.

Also provided in accordance with aspects of the invention are pharmaceutical compositions useful as natriuretics, diuretics, vasodilators and/or modulators of the renin-angiotensin-aldosterone system, which compositions containing the above-recited analog peptide compounds, including their amides and esters, and the nontoxic addition salts thereof, together with a pharmaceutically acceptable liquid, gel or solid carrier Administration of therapeutically effective doses of these compositions can provide effective delivery of the above-recited biological activities to mammalian hosts.

Additional aspects of the present invention provide methods for producing such compounds and compositions, and methods for using the compounds and compositions as therapeutic agents.

BRIEF DESCRIPTION OF THE DRAWINGS

FIG. 2 is a graph which depicts competitive displacement receptor binding of compounds of the present invention using cultured bovine aortic smooth muscle (BASM) cells; and FIG. 3 depicts the in vivo diuretic activities of selected compounds of the present invention in anesthetized rats, wherein FIG. 3A portrays the diuretic activity of the analog peptide identified as AP25, FIG. 3B portrays the diuretic activity of the analog peptide identified as AP20, FIG. 3C portrays the diuretic activity of the analog peptide identified as AP21, FIG. 3D portrays the diuretic activity of the analog peptide identified as AP37, FIG. 3E portrays the diuretic activity of the analog peptide identified as AP101, FIG. 3F portrays the diuretic activity of the analog peptide identified as AP319, FIG. 3G portrays the diuretic activity of the analog peptide identified as AP324, and FIG. 3H portrays the diuretic activity of the analog peptide identified as AP54.

FIG. 4 gives a list of various compounds of the invention.

FIG. 5 gives a list of various compounds which are similar to those of the invention, but which are outside its scope.

MODES OF CARRYING OUT THE INVENTION

Figure 1:
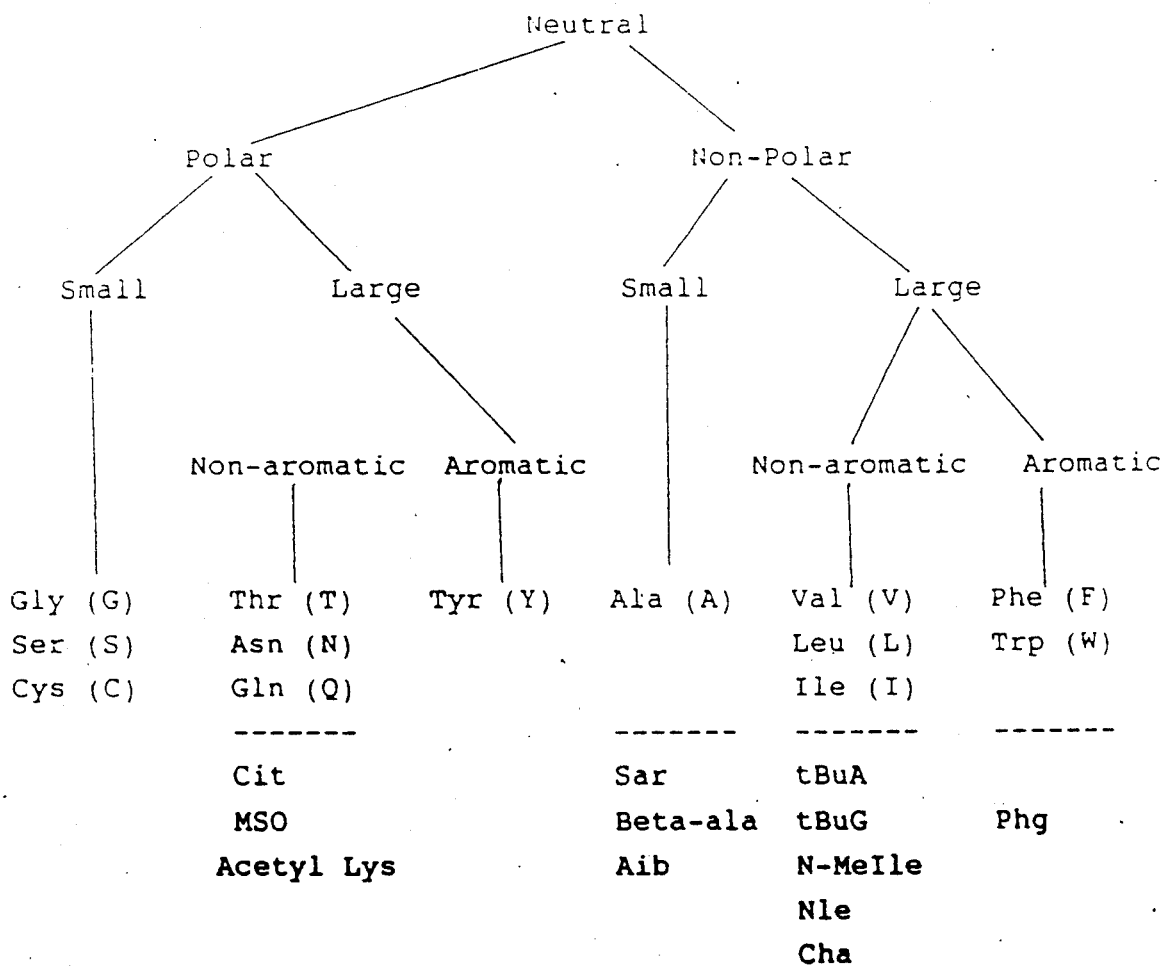
FIG. 1 schematically outlines the classification of amino acids as used herein.

In accordance with the present invention, a class of novel analogs of native Atrial Natriuretic Peptide (ANP) compounds is provided which is capable of exhibiting or modulating the natriuretic, diuretic and/or vasorelaxant activity of the native peptides in mammals in vivo.

The sequence of amino acid residues of the present synthetic analog compounds, including the core pentapeptide, and preferred embodiments thereof, are defined in terms of amino acids of certain characteristics of particular subclasses.

Amino acid residues can be generally subclassified into four major subclasses as follows and as shown in FIG. 1.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, sub-classification according to the foregoing scheme is as follows (see also FIG. 1).

Acidic: Aspartic acid and Glutamic acid;
Basic/noncyclic: Arginine, Lysine;
Basic/cyclic: Histidine;
Neutral/polar/small: Glycine, Serine and Cysteine;
Neutral/polar/large/nonaromatic: Threonine, Asparagine, Glutamine;
Neutral/polar/large/aromatic: Tyrosine;
Neutral/nonpolar/small: Alanine;
Neutral/nonpolar/large/nonaromatic: Valine, Isoleucine, Leucine, Methionine;
Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-ala), or other omega-amino acids, such as 4-amino butyric and so forth, alpha-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definition,
Sar and beta-ala are neutral/nonpolar/small;
t-BuA, t-BuG, N-MeIle, Nle and Cha are neutral/nonpolar/large/nonaromatic;
Orn is basic/noncyclic;
Cya is acidic;
Cit, Acetyl Lys, and MSO are neutral/polar/large/nonaromatic; and
Phg is neutral/nonpolar/large/aromatic.
See, also, FIG. 1.

The various omega-amino acids are classified according to size as neutral/nonpolar/small (beta-ala, 4-aminobutyric) or large (all others).

Other amino acid substitutions for those encoded in the gene can also be included in peptide compounds within the scope of the invention and can be classified within this general scheme.

The nomenclature used to describe ANP analog compounds of the present invention follows the conventional practice wherein the amino group is assumed to the left and the carboxy group to the right of each amino acid in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+{}_2$ and C-terminal-$O^-$ at physiological pH are understood to be present though not necessarily specified and shown, either in specific examples or in generic formulas. In the peptides shown, each encoded residue where appropriate is represented by a single letter designation, corresponding to the trivial name of the amino acid, in accordance with the following conventional list:

| Amino Acid | One-Letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The amino acids not encoded genetically are abbreviated as indicated above.

In the specific peptides shown in the present application, the L-form of any amino acid residue having an optical isomer is intended unless otherwise expressly indicated by a dagger superscript ( ). While the residues of the invention peptides are normally in the natural L optical isomer form, one or two, preferably one, amino acid in addition to as well as instead of $AA_9$ and/or $AA_{12}$, may be replaced with the optical isomer D form (including embodiments where $AA_9$ and $AA_{12}$ are both L).

Free functional groups, including those at the carboxy- or amino-terminus, can also be modified by amidation, acylation or other substitution, which can, for example, change the solubility of the compounds without affecting their activity.

In particular, it has been discovered that carboxyl terminal amide-modified analogs of Atrial Natriuretic Peptides are particularly potent and therefore preferred embodiments of the present invention. In general, the nitrogen atom of the amido group, covalently bound to the carbonyl carbon, will be $NH_2$, $-NHR'$, or $NR'R''$, wherein $R'$ and $R''$ are straight or branched chain alkyl or alkyl acyl of 1–10C, preferably 1–6C, including these groups wherein 1–2 carbons are replaced by nitrogen, oxygen or sulfur atoms. Representatives of such amido groups are: $-NH_2$, $-NHCH_3$, $-N(CH_3)_2$, $-NHCH_2CH_3$, $-NHC_6H_5$, $-NHCH_2CH(CH_3)_2$, $-NHCH_2CH(CH_3)CH_2CH_3$, $-NHCH_2CH_2OH$, $-NHCH_2OCH_2CH_3$ and $-N(CH_3)CH_2CH_2SCH_2CH_3$, among others.

In forming amidated analogs of the present invention, the analog compounds can be synthesized directly, for example using Boc-$AA_x$-pMBHA-Resin or Boc-$AA_x$-BHA-Resin, wherein $AA_x$ is the selected carboxy-terminal amino acid of the desired analog compound as described in further detail below. Alternatively, the analog compounds of the present invention can be chemi-cally or enzymatically amidated subsequent to peptide synthesis using means well known to the art, or prepared by standard solution-phase peptide synthesis protocols.

PREFERRED EMBODIMENTS

A. The Core Pentapeptide

The compounds of the invention all contain the pentapeptide core sequence:

$AA_8$-$AA_9$-$AA_{10}$-$AA_{11}$-$AA_{12}$, wherein each of $AA_8$ and $AA_{11}$ is, independently:

a basic/noncyclic; or a neutral/nonpolar/small; or a neutral/polar/large/nonaromatic amino acid residue;

in addition, $AA_8$ can be a neutral/nonpolar/large/nonaromatic amino acid;

$AA_9$ is a neutral/nonpolar/nonaromatic amino acid residue in the D or L configuration;

$AA_{10}$ is an acidic amino acid residue; and $AA_{12}$ is a neutral/nonpolar/large/nonaromatic amino acid residue in the D or L configuration, or is a covalent bond.

The most preferred sequence of this core is R(I/M)-DRI, wherein all residues are in the L configuration and the amino acid residues contained within the parentheses are alternatives. Next in preference are those sequences wherein only one of the R(I/M)DRI residues has been substituted by an alternative residue within the above definitions. Preferred substitutions are:

For $AA_8$, instead of R: K, Acetyl Lys, A, Q, N, L or Nle;

for $AA_9$, instead of I/M: V, V , L, L , I , M , t-BuA, t-BuG, or Cha;

for $A_{10}$, instead of D: E or Cya;

for $A_{11}$, instead of R: K, NeAcetyl Lys, A, Q, N, Orn, or Cit;

for $A_{12}$, instead of I: M, M , V, V , L, L , I , N-MeIle, t-BuA, or a covalent bond.

Particularly preferred are those embodiments wherein this sequence is selected from the group consisting of:

| | | |
|---|---|---|
| A(I/M)DRI | RM DRI | R(I/M)DRL |
| K(I/M)DRI | RLDRI | R(I/M)DRM |
| NE Acetyl Lys (I/M)DRI | | |
| Q(I/M)DRI | R(I/M)ERI | R(I/M)DRM |
| RVDRI | R(I/M)DKI | R(I/M)DRI |
| RI DRI | R(I/M)DQI | R(I/M)DRV |

More than one alteration from the naturally occurring RIDRI or RMDRI sequence is within the scope of the invention, but less preferred. Particularly favored subsets of this group include those wherein glutamic replaces aspartic as $AA_{10}$, in addition to another substitution.

B. Embodiments of $Z_1$

Preferred forms of $Z_1$ include in addition to non-amino acid hydrophobic residues, described below, peptides of 1–5, more usually 1–3, amino acids or the des$NH_2$ forms thereof, wherein the C-terminal amino acid is hydrophobic, i.e. neutral and nonpolar, and most particularly is Phe or des$NH_2$-Phe. Preferred embodiments of $Z_1$ include R-S-S-C-F, R-S-S-A-F, Y-A-F, R-C-F, S-C-F, A-F, C-F, and F or des$NH_2$-F, i.e., those wherein the C-terminal end amino acid residue is F, and the upstream residues are selected from Y, A, C, S, and R.

Preferred nonpeptide-derived forms of $Z_1$ include organic substituent groups which are generally non-toxic, hydrophobic and relatively large or bulky when compared to substituent groups ordinarily found with amino acid residues.

One class of presently preferred organic substituent groups can be represented by the general formula:

wherein $R_1$ is an organic hydrophobic group. Included in this formula are 2-substituted acetyl, 3-substituted propionyl, and 4-substituted butyryl groups, wherein the substitutions to these groups include the general class of neutral, hydrophobic mono- and polycyclic aromatic or saturated ring systems, and/or halogens. Other classes have the general formulas $R_1$—CO—C— and $R_1$—O—. Representative examples of the preferred substituent groups include:

9 fluorenylmethyloxycarbonyl (FMOC)

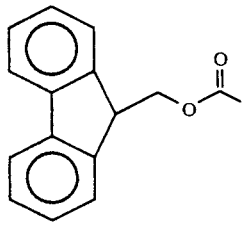

benzyloxycarbonyl (CBZ)

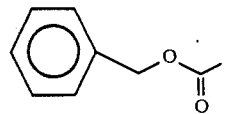

2-(2'-(6'-methoxynaphthyl)) propionyl 2-(2'-(6'-MeONAP)

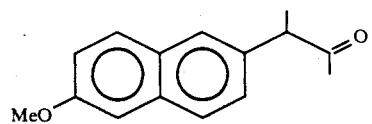

3,3 Diphenylpropionyl (DPP)

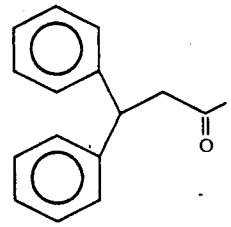

3 Biphenylacetyl (BPA)

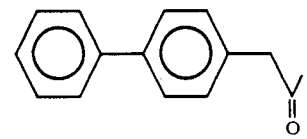

3,3,3 Triphenylpropionyl (TPP)

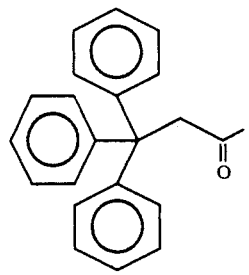

Cyclohexylacetyl (CHA)

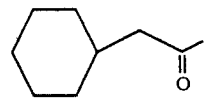

3-Indolepropionyl (3-1P)

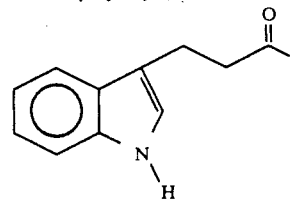

4-Indolebutyryl (4-IB)

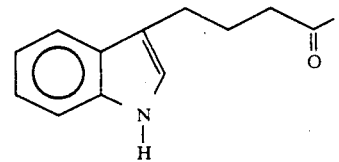

1-Adamantylacetyl (AA)

1-Naphthylacetyl (1-NA)

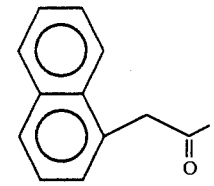

2-Naphthylacetyl (2-NA)

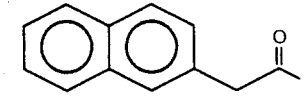

1-Naphthoxyacetyl (1-NOA)

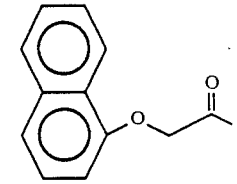

2-Naphthoxyacetyl (2-NOA)

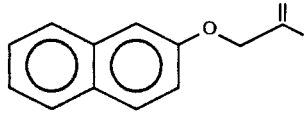

Dibenzylacetyl (DBA)

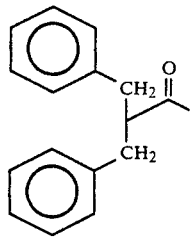

bis (1'-naphthylmethyl) acetyl (BNMA)

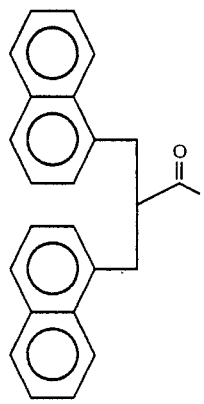

2-naphthylthioacetyl (2-NTA)

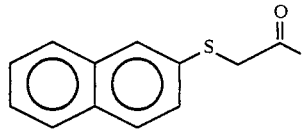

3-phenoxypropionyl (3-POP)

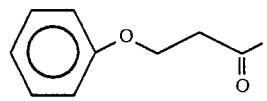

2-Naphthoyl (2-NYL)

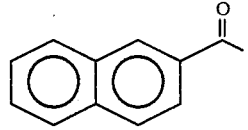

2-naphtoxy (2-NO)

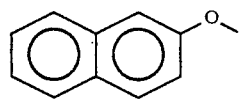

2-naphthyl (2-NL)

2-halo acetyl phenylalanyl, e.g. 2ClAF or 2BrAF
ClCH$_2$CO—F— or BrCH$_2$CO—F—

-continued
2-halo phenylacetyl, e.g., 2ClPA or 2BrPA

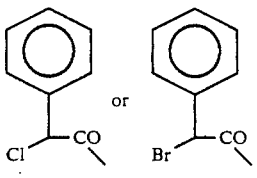

groups. Particularly preferred are NA, NOA, and NYL.

The 2-halo forms are thought to have the possibility to bind covalently to the clearance receptor as "suicide" binders.

C. Embodiments of $Z_2$

In the compounds of the invention, $Z_2$ provides a spacer element separating $AA_8$ from the hydrophobic portion of $Z_1$. The linker $Z_2$ must be capable to achieve a distance between $AA_8$ and the hydrophobe of about between 4.5 and 15 angstroms, corresponding to 3–9 atoms in a normally extended chain. Of course, longer linkers can be used provided their 3-dimensional conformations permit this spacing distance to be accommodated.

Preferred embodiments for $Z_2$ are selected from the group consisting of (a) $(AA)_a$ wherein AA is an amino acid and a is 1 or 2, especially wherein each AA is selected from G, S, A, Sar, and Aib;

(b) —$(P)_n$—$(CO)_x$— wherein x is 0 or 1, n is 1-6, and P is CH$_2$, wherein 1-2 of said —CH$_2$— groups can be replaced by NH, provided N-N does not occur; and (c) —$(Q)_m$—B—$(Q)_m$—$(CO)_x$— wherein x is 0 or 1, each m is independently 0–3 but the sum of both m is 5 or less; Q is CH$_2$ or NH, with the proviso that —N—N— does not occur, and B is a saturated or unsaturated five- or six-membered ring optionally containing an N heteroatom. B can be joined to Q either 1, 4 or 1, 3. Particularly preferred is p-aminophenyl acetyl (4-APA).

D. Embodiments of $Z_3$

Preferred for $Z_3$ are NH$_2$, NHR', and the amide or alkyl amide of peptide residues of 1-3 amino acids. Especially preferred among the embodiments which are peptide residues are those wherein the amino acids are selected from G, A, and S. In particular, however, when $AA_{12}$ is a covalent bond, $Z_3$ should be in the alkyl amidated form, e.g., —NHR' wherein R' is 2–10C.

E. Non-Peptide Linkages

In one embodiment of the invention, the amide linkages (—CO—NH—) within the core pentapeptide or those described above within $Z_1$ and/or $Z_2$ and/or $Z_3$ can be replaced with other types of linkages such as —CH$_2$NH—, —CH$_2$—S—, —CH$_2$CH$_2$—, —CH=CH— (cis and trans), —COCH$_2$—, —C(OH)CH$_2$— and —CH$_2$SO—, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F. in "Chemistry and Biochemistry of Amino Acids Peptides and Proteins", B. Weinstein, eds., Marcel Dekker, New York, p. 267 (1983) (general review); Morley, J. S. *Trends Pharm Sci* (1980) pp. 463-468 (general review); Hudson, D. et al *Int J Pept Prot Res* (1979) 14:177-185 (—CH$_2$NH—, —CH$_2$CH$_2$—); Spatola, A. F. et al, *Life Sci* (1986) 38:1243-1249 (—CH$_2$—S); Hann, M. M. *J Chem Soc Perkin Trans I* (1982) 307-314 (—CH—CH—, cis and trans); Almquist, R. G., et al, *J Med Chem* (1980) 23:1392-1398(—COCH$_2$—); Jennings-White, C. et al *Tetrahedron Lett* (1982) 23:2533 (—COCH$_2$—); Szelke, M., et al, European Appln EP 45665 (1982) CA: 97: 39405 (1982) (—CH(OH)CH$_2$—); Holladay, M. W. et al *Tetrahedron Lett* (1983) 24:4401-4404 (—C(OH)CH$_2$—); and Hruby, V. J. *Life Sci* (1982) 31:189-199 (—CH$_2$—S—). Particularly preferred is —CH$_2$NH—.

Synthesis

Compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-Asn-OH, Boc-Ser-OH, Boc-Phe-OH, Boc-Arg-OH or Boc-Tyr-OH (i.e., selected ANP analog carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart, et al, *Solid-Phase Peptide Synthesis* (1969) W. H. Freeman Co., San Francisco and Merrifield, *J Am Chem Soc* (1963) 85:2149-2154. These and other methods of peptide synthesis are also exemplified by U.S. Pat. Nos. 3,862,925, 3,842,067, 3,972,859, and 4,105,602.

The synthesis may use manual techniques or automatically employing, for example, an Applied BioSystems 430A Peptide Synthesizer (Foster City, Calif.) or a Biosearch SAM II automatic peptide synthesizer (Biosearch, Inc. San Rafael, Calif.), following the instructions provided in the instruction manual supplied by the manufacturer.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds. Since the peptide sequences are relatively short, recombinant production is facilitated.

Administration and Use

Compounds of the present invention are shown to have natriuretic, diuretic and hypotensive activity in the intact mammal, and may possess vasorelaxant activity or inhibit the release of aldosterone and renin.

Thus these compounds, and compositions containing them, can find use as therapeutic agents in the treatment of various edematous states such as, for example, congestive heart failure, nephrotic syndrome and hepatic cirrhosis, pulmonary disease, in addition to hypertension and renal failure due to ineffective renal perfusion or reduced glomerular filtration rate.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 1000 mcg/kg, more usually 0.1 to 1000 mcg/kg of the host body weight. Alternatively, dosages within these ranges can be administered by constant infusion over an extended period of time until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%-95% of active ingredient, preferably 25%-70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme or receptor activity and thus inhibiting these enzymes or receptors. When employed in this manner, such compounds can be delivered as admixtures with other active compounds or can be delivered separately, for example, in their own carriers.

Compounds of the present invention can also be used for preparing antisera for use in immunoassays employing labeled reagents, usually antibodies. Conveniently, the polypeptides can be conjugated to an antigenicity-conferring carrier, if necessary, by means of dialdehydes, carbodiimide or using commercially available linkers. These compounds and immunologic reagents may be labeled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The following examples are provided by way of illustration, rather than implying any limitation of the subject invention.

EXAMPLES

In the experimental disclosure which follows, the amino acid sequence of chemically synthesized ANP analog compounds are numbered from the amino-terminal arginine residue corresponding to the arginine residue found at position 1 in the native rat-derived Atrial Natriuretic Peptide sequence disclosed in Atlas, S., et al, *Nature* (1984) 309:717-719.

I. Chemical Synthesis of Atrial Natriuretic Peptide Analog Compounds

A. Synthesis Procedures

Compounds of the present invention were synthesized by solid-phase techniques performed manually or, alternatively, on an Applied BioSystems 430A Peptide Synthesizer (Foster City, Calif.) or a Biosearch Sam II automated peptide synthesizer (Biosearch, San Rafael, Calif.) using t-Boc amino acids in accordance with the instructions of the manufacturer.

Procedure A

Preparation of Boc-AA$_1$ . . . AA$_{n-1}$-AA$_n$-Resin Hydroxymethyl Polystyrene Ester One gram of selected Boc-AA$_n$-O-Polystyrene-Resin (0.2-0.6 mmole/g resin) (obtainable from, e.g., Peninsula Labs, Inc.) is treated according to schedule A for incorporation of the Boc-AA$_{n-1}$-OH.

Schedule A

1) Wash 3x with dichloromethane (CH$_2$Cl$_2$);
2) Treat for 1 min. with TFA:CH$_2$C$_2$:ethane dithiol (EDT) (45:50:5 by volume);
3) Treat for 20 min. with TFA:CH$_2$C$_2$:EDT (45:50:5) by volume;
4) Wash 3x with CH$_2$C$_2$;
5) Treat 2x for 1 min. 10% (V/V) Diisopropylethylamine (DIPEA) in CH$_2$C$_2$;
6) Wash 2x with CH$_2$C$_2$;
7) Wash 2x with methanol (MeOH);
8) Repeat (5-7) once;
9) Wash 3x with CH$_2$C$_2$;
10) Add 1-6 equivalents of preformed symmetrical anhydride of the suitably protected Boc-amino acid dissolved in CH$_2$C$_2$ or dimethyl formamide (DMF)/CH$_2$C$_2$ (50:50 volume), (Boc-Asn-OH, Boc-Gln-OH and Boc-Arg(TOS)-OH were coupled as active esters using N-hydroxybenzotriazole);
11) Wash 2x with CH$_2$C$_2$;
12) Wash 2x with 10% DIPEA;
13) Wash 2x with CH$_2$C$_2$;
14) Wash 2x with MeOH;
15) Wash 2x with CH$_2$C$_2$;
16) Repeat steps (11-15) once;
17) Test by ninhydrin reaction according to Kaiser et al., *Anal. Biochem.* 34:595 (1970). If the coupling reaction was incomplete, repeat steps (10-16) or, alternatively, cap synthesis using N-acetyl imidazole (0.30M in DMF) or an excess of acetic anhydride in CH$_2$C$_2$.

Procedure B

Preparation of Boc-AA$_n$-p-Methylbenzhydrylamine resin

The selected Boc-AA$_n$-OH is attached to a p-Methylbenzhydrylamine (pMBHA) resin via N,N'-dicyclohexylcarbodiimide, as described below.

Schedule B

1) Wash the pMBHA HCl resin;
2) Wash the resin 2x with 10% (V/V) DIPEA in CH$_2$Cl$_2$;
3) Wash 2x with CH$_2$C$_2$;
4) Wash 2x with MeOH;
5) Wash 2x with CH$_2$C$_2$;
6) Add 1-6 equivalents of preformed symmetrical anhydride of the suitably protected Boc-amino acid dissolved in CH$_2$C$_2$, with reaction time of 0.5-24 hrs.

Unreacted amino groups are acetylated with 0.30M N-acetylimidazole:DMF, or acetic anhydride:CH$_2$C$_2$. The following examples demonstrate the chemical synthesis of representative analog ANP compounds (identified as AP#) which illustrate certain aspects of the present invention.

EXAMPLE 1

\* AP1

R-S-S-C-F-G-G-R-I-D-R-I-G-A-Q-S-G-C—N-S-F-R-Y

One gm of Boc-Tyr(2BrZ)-0-Resin (0.54 meq/gm, Peninsula Labs Inc., Belmont, Calif.) was subjected to procedure A with the required sequence of amino acids (introduced in order as Boc-Arg(Tos)-OH, Boc-Phe-OH, Boc-Ser(Bzl)-OH, Boc-Asn-OH, Boc-Cys(4-CH$_3$Bzl)-OH, Boc-Gly-OH, Boc-Ser(Bzl)-OH, Boc-Gln-OH, Boc-Ala-OH, Boc-Gly-OH, Boc-Ile-OH 1/2H₂O, Boc-Arg(Tos)-OH, Boc-Asp(OBzl)-OH, Boc-Ile-OH 1/2H₂O, Boc-Arg(Tos)-OH, Boc-Gly-OH, Boc-Gly-OH, Boc-Phe-OH, Boc-Cys(4-CH₃Bzl)-OH, Boc-Ser(Bzl)-OH, Boc-Ser(Bzl)-OH, Boc-Arg(Tos)-OH). The protected peptidyl resin was treated with TFA:CH₂C₂ EDT (45:50:5 v/v/v) for 1 min., then 20 min. and washed 3 times with CH₂C₂ and 2 times with MeOH to give the TFA salt of the peptidyl resin, and dried in vacuo.

The peptidyl resin was then suspended in anhydrous hydrogen fluoride (HF) containing 10% anisole, 2% ethyl methyl sulfide for 30 min. at =10° C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethyl ether. The peptide was extracted from the mixture with 2.0M acetic acid, diluted with H₂0 and lyophilized, to give the unoxidized sulfhydryl peptide.

The crude peptide was dissolved in deoxygenated 0.01M ammonium acetate (NH₄OAc), pH 7.9, to 0.5 mg/ml and then oxidized by dropwise addition of a slight excess of 0.01M potassium ferricyanide (KCN) solution, stirred 20 minutes and adjusted to pH 5 with acetic acid. The peptide solution was treated with DOWEX AG3×4 anion exchange resin, filtered, diluted with H₂O and lyophilized to give the crude cyclized peptide.

Purification of the peptide was achieved by desalting on Sephadex® G-25F (Pharmacia Fine Chemicals) using 0.5M AcOH as eluant, followed by ion exchange chromatography on CM-Sepharose® (Pharmacia Fine Chemicals) or CM-cellulose (Whatman) using an elution gradient generated by addition of 300 mM NH₄OAc, pH 6.5, to a solution of 10 mM NH₄OAc, pH 4.5. Fractions were collected having a minimum 97% purity, as judged by reversed phase HPLC, then pooled and lyophilized from H₂O several times to yield the purified AP1 acetate salt.

EXAMPLE 2·

* AP2

R-S-S-C-G-R-I-D-R-I-G-A-Q-S-G-C-N-S-F-R-Y

One gm of Boc-Tyr(2BrZ)-0-Resin (0.54 meq/gm, Peninsula Labs Inc., Belmont, Calif.) was subjected to procedure A with the required sequence of amino acids (introduced in order as Boc-Arg(Tos)-OH, Boc-Phe-OH, Boc-Ser(Bzl)-OH, Boc-Asn-OH, Boc-Cys(4-CH₃Bzl)-OH, Boc-Gly-OH, Boc-Ser(Bzl)-OH, Boc-Gln-OH, Boc-Ala-OH, Boc-Gly-OH, Boc-Ile-OH 1/2H₂O, Boc-Arg(Tos)-OH, Boc-Asp(OBzl)-OH, Boc-Ile-OH 1/2H₂O, Boc-Arg(Tos)-OH, Boc-Gly-OH, Boc-Cys(4CH₃Bzl)-OH, Boc-Ser(Bzl)-OH, Boc-Ser(Bzl)-OH, Boc-Arg(Tos)-OH). The protected peptidyl resin was treated with TFA:CH₂C₂:EDT (45:50:5 v/v/v) for 1 min., then 20 min. and washed 3 times with CH₂C₂, 2 times with MeOH and dried in vacuo to give the TFA salt of the peptidyl resin.

The peptidyl resin was then suspended in anhydrous HF containing 10% anisole, 2% ethyl methyl sulfide for 30 min. at −10° C. and 30 min. at 0° C. The HF was removed by evaporation under vacuum and the peptide/resin mixture was suspended in diethyl ether. The peptide/resin mixture was washed twice with diethyl ether, twice with chloroform, and twice with diethyl ether. The peptide was extracted with 2.0M acetic acid and lyophilized, to give the unoxidized sulfhydryl peptide.

The crude peptide was dissolved in deoxygenated 0.01M NH₄OAc, pH 7.9, to 0.5 mg/ml and then oxidized by dropwise addition of a slight excess of 0.01M KCN solution, stirred for 20 minutes and adjusted to pH 5 with acetic acid. The peptide solution was treated with DOWEX AG3×4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc, pH 6.5, to a solution of 10 mM NH₄OAc, pH 4.5. Fractions were collected having a minimum 97% purity, as judged by reversed phase HPLC, then pooled and lyophilized from H₂O several times to yield the purified AP2 acetate salt.

EXAMPLE 3

* AP3

R-S-S-C-F-G-G-R-I-D-R-I-G-A-Q-S-C-N-S-F-R-Y

One gm of Boc-Tyr(2BrZ)-O-Resin (0.54 meq/gm, Peninsula Labs Inc., Belmont, Calif.) was subjected to procedure A with the required sequence of amino acids (introduced in order as Boc-Arg(Tos)-OH, Boc-Phe-OH, Boc-Ser(Bzl)-OH, Boc-Asn-OH, Boc-Cys(4-CH₃Bzl)-OH, Boc-Ser(Bzl)-OH, Boc-Gln-OH, Boc-Ala-OH, Boc-Gly-OH, Boc-Ile-OH 1/2H₂O, Boc-Arg(Tos)-OH, Boc-Asp(OBzl)-OH, Boc-Ile-OH ½/H₂O, Boc-Arg(Tos)-OH, Boc-Gly-OH, Boc-Gly-OH, Boc-Phe-OH, Boc-Cys(4CH₃Bzl)-OH, Boc-Ser(Bzl)-OH, Boc-Ser(Bzl)-OH, Boc-Arg(Tos)-OH). The protected peptidyl resin was treated with TFA:CH₂C₂:EDT (45:50:5 v/v/v) for 1 min., then 20 min. and washed 3 times with CH₂C₂ and twice with MeOH to give the TFA salt of the peptidyl resin and dried in vacuo.

The peptidyl resin was then suspended in anhydrous HF containing 10% anisole, 2% ethyl methyl sulfide for 30 min. at −10 ° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M KCN solution, stirred 20 minutes and adjusted to pH 5 with acetic acid. The peptide solution was treated with DOWEX AG3×4 anion exchange resin, filtered, diluted with H₂O and lyophilized to give the crude cyclized peptide.

Purification of the peptide was achieved by desalting on Sephadex® G-25F using 0.5M AcOH· as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP3 acetate salt.

EXAMPLE 4

\* AP4

R-S-S-C-F-G-G-R-I-D-R-I-G-A-C—N-S-F-NH₂

One gm of Boc-Phe-pMBHA resin, obtained using schedule B, was subjected to procedure A with the required sequence of amino acids (introduced in order as Boc-Ser(Bzl)-OH, Boc-Asn-OH, Boc-Cys(4-CH₃Bzl)-OH, Boc-Ala-OH, Boc-Gly-OH, Boc-Ile-OH.1/2H₂O, Boc-Arg(Tos)-OH, Boc-Asp(OBzl)-OH, Boc-Ile-OH.1/2H₂O, Boc-Arg(Tos)-OH, Boc-Gly-OH, Boc-Gly-OH, Boc-Phe-OH, Boc-Cys(4-CH₃Bzl)-OH, Boc-Ser(Bzl)-OH, Boc-Ser(Bzl)-OH, Boc-Arg(Tos)-OH). The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M K₃Fe(CN)₆ stirred for 20 minutes and adjusted to pH 5 with acetic acid. The peptide solution was treated with DOWEX AG3×4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP4 acetate salt.

Following the procedures outlined in Examples 1-4 (to produce analog peptides AP1-4) with appropriate modification, the ANP analogs set forth in part A of FIG. 4 are synthesized.

The following examples demonstrate the chemical synthesis of representative organic substituent group modified analog peptide compounds (identified as AP#) which illustrate certain aspects of the present invention.

EXAMPLE 306

\* AP306

(2—Naphthylacetyl)-G-G-R-I-D-R-I-G-A-NH₂

One gm of Boc-Ala-pMBHA resin (0.4 meq/gm), obtained using schedule B, was subjected to procedure A with the required sequence of amino acids and Amino-terminal substituent group (introduced in order as Boc-Gly-OH, Boc-Ile-OH 1/2H₂O, Boc-Arg(Tos)-OH, Boc-Asp(OBzl)OH, Boc-Ile-OH 1/2H₂O, Boc-Arg(Tos)-OH, Boc-Gly-OH, Boc-Gly-OH, 2-Naphthlyacetic acid). The protected peptidyl resin was washed 3 times with CH₂C₂ and 3 times with MeOH and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in ethyl ether. After transfer to a fritted funnel, the peptide/resin mixture was washed twice with ethyl ether, once with chloroform, once with ethyl ether, once with chloroform and once again with ethyl ether. The peptide was then extracted from the mixture with 2.0M acetic acid, diluted with H₂O and lyophilized.

Purification of the peptide was achieved by ion exchange chromatography on CM-Sepharose® (Pharmacia) using an elution gradient generated by addition of 100 mM NH₄OAc, pH 6.5, to a solution of 10 mM NH₄OAc, pH 4.5. Fractions were monitored at 254 nm and analyzed by reversed phase HPLC. Fractions having a minimum 97% purity were pooled and lyophilized from H₂O several times to yield the purified AP306 acetate salt.

EXAMPLE 307

\* AP307

(2-Naphthoxyacetyl)-NH(CH₂)₄CO-R-I-D-R-I-NH₂

One gm of Boc-Ile-pMBHA resin (0.4 meq/gm), obtained using schedule B, was subjected to procedure A with the required sequence of amino acids and Amino-terminal substituent group (introduced in order as Boc-Arg(Tos)-OH, Boc-Asp(OBzl)-OH, Boc-Ile-OH ½H₂O, Boc-Arg(Tos)-OH, Boc-NH(CH )4COOH, 2—Naphthoxyacetic acid). The protected peptidyl resin was washed three times with CH₂C₂ and three times with MeOH and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in ethyl ether. After transfer to a fritted funnel, the peptide/resin mixture was washed twice with ethyl ether, once with chloroform, once with ethyl ether, once with chloroform and once again with ethyl ether. The peptide was then extracted from the mixture with 2.0M acetic acid, diluted with H₂O and lyophilized.

Purification of the peptide was achieved by ion exchange chromatography on CM-Sepharose® (Pharmacia) using an elution gradient generated by addition of 100 mM NH₄OAc, pH 6.5, to a solution of 10 mM NH₄OAc, pH 4.5. Fractions were monitored at 254 nm and analyzed by reversed-phase HPLC. Fractions having a minimum 97% purity were pooled and lyophilized from H₂O several times to yield the purified AP307 acetate salt.

Following the procedures outlined in Examples 306 and 307 (to produce analog peptides AP306 and AP307) with appropriate modification, the ANP analogs set forth in part B of FIG. 4 were synthesized. In the figure, the following abbreviations are used:

AA=Adamantylacetyl
BPA=Biphenylacetyl
CHA=Cyclohexylacetyl
DBA=Dibenzylacetyl
DPP=Diphenylpropionyl
IB=Indolebutyryl
IP=Indoleproprionyl NA = Naphthylacetyl
NL = Naphthyl
NM = Naphthylmethyl
NO = Naphthoxy
NOA = Naphthoxyacetyl
NTA = Naphthylthioacetyl
NYL = Naphthoyl
POP = Phenoxypropionyl
TPP = Triphenylpropionyl
MeONAP = Methoxynaphthylpropionyl In each of the starred examples, amino acid analysis demonstrated that the appropriate amino acid sequence of the peptide was obtained.

II. Biological Testing

Biological activity data for selected analog Atrial Natriuretic Peptides (ANPs) which were synthesized as disclosed above are presented below as biochemical, isolated tissue and whole mammal bioassays.

Without intending to be bound by any theory, it is believed that the activity of the ANP analog compounds of the invention is due to their affinity for receptors in the kidney and other sites which are responsible for influencing the clearance of the endogenous ANPs. The following in vitro biological data show that the analog compounds of the invention compete with an iodinated native ANP molecule for binding to receptors from cultured bovine aortic smooth muscle (BASM) cells, and bovine endothelia (BAE) cells. This competition is, evidently, diagnostic for the binding to the relevant clearance receptors. This correlation is confirmed by data which demonstrate that analogs active in the competitive binding assay (subsection A) are able to cause diuresis and natriuresis in anesthetized rats and dogs and to lower blood pressure in anesthetized rats (subsection B). However, the analogs do not cause diuresis or natriuresis in isolated kidney, but potentiate the effect of "natural" ANP in the isolated tissue (subsection C). In addition, the analogs of the invention show reduced cyclic GMP activity, an activity which is a hallmark of the direct biological function of ANP.

The results below demonstrate that a wide range of peptides within the scope of the invention test positive in an in vitro assay, which is then confirmed, using representative peptides, as a model for natriuretic/diuretic and vasodilator activity in vivo. It is also postulated by the inventors some, if not many of the peptides and peptide analogs disclosed herein will have oral activity as well.

A. Receptor binding assays

Specific ANP receptor sites have been identified on target tissues, such as kidney, adrenal, blood vessels, and cultured cells. Napier, M. A., et al, Proc Nat Acad Sci USA (1984) 81:5946-5940; DeLean, A., et al, Endocrinology (1984) 115:1636-1638; Schenk, D. B. et al, Biochem Biophys Res Comm (1985) 127:433-442. Since the binding of ANP or ANP analogs to these specific receptor sites is presumptively a prerequisite of biological activity, binding of ANP analogs to these receptors is considered predictive of biological activity.

An assay has been developed, generally in accordance with the disclosure of Schenk, supra, and Scarborough, R. M., et al, J Biol Chem (1986) 261:12960-12964, which evaluates the ability of ANP analogs to compete with labeled native ANP for binding to cultured BASM and BAE cells. This native ANP, having the amino acid sequence:

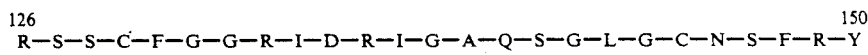

126
R—S—S—C—F—G—G—R—I—D—R—I—G—A—Q—S—G—L—G—C—N—S—F—R—Y
150 was iodinated on the carboxy-terminal Y residue and is identified as ($^{125}$I)-rANP(126-150). Analogous "competitive displacement" receptor binding assays are considered commonplace in the art for examining specific ligand-receptor interactions. An example of the results of this ANP-receptor binding assay is presented in FIG. 1.

In this assay, 0.5 nM ($^{125}$I)-rANP(126-150) was incubated in each individual sample of BASM cells in the presence of varying amounts of labeled rANP(126-150) or a compound having the amino acid sequence:

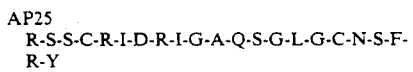

AP25
R-S-S-C-R-I-D-R-I-G-A-Q-S-G-L-G-C-N-S-F-R-Y

AP37 C-F-G-G-R-I-D-R-I-G-A-C-NH$_2$
AP101 A-F-G-G-R-I-D-R-I-G-A-NH$_2$ or
AP132 (desNH$_2$-F)-G-G-R-I-D-R-I-NH$_2$ As shown in FIG. 2, increasing concentrations of rANP(126-150), or analog peptides AP25, AP37, AP101 or AP132, effectively prevent ($^{125}$I)-rANP(126-150) binding to BASM cell-associated receptors. The concentration of unlabeled peptide at which 50% of maximal ($^{125}$I)-rANP(126-150) binding is displaced is called Ki(app) and reflects receptor-binding affinity. Therefore, hypothetical peptide A, with a Ki(app) = 100 nM, displays substantially weaker interaction with a receptor than hypothetical peptide B with a Ki(app) = 10 nM. Assuming these ANP analogs act at one or more ANP receptor sites, then increased receptor affinity should reflect increased biological potency.

Tables 1A-1F present data which compare the concentrations at which analog compounds of the invention displace ($^{125}$I)-rANP(126-150) binding from specific receptor sites on BASM or BAE cells. As will be shown below, these data correlate with in vivo activity characteristic of native ANP.

TABLE 1A

| Peptide | Sequence | Ki(app)(nM) |
|---|---|---|
| rANP(126-150) | R—S—S—C—F—G—G—R—I—D—R—I—G—A—Q—S—G—L—G—C—N—S—F—R—Y | 7.26 |
| AP23 | R—S—S—C—G—G—R—I—D—R—I—G—A—Q—S—G—L—G—C—N—S—F—R—Y | 7.76 |
| AP24 | R—S—S—C—G—R—I—D—R—I—G—A—Q—S—G—L—G—C—N—S—F—R—Y | 25.2 |
| AP25 | R—S—S—C—R—I—D—R—I—G—A—Q—S—G—L—G—C—N—S—F—R—Y | 8.62 |
| AP54 | R—S—S—C—I—D—R—I—G— | >200 |

TABLE 1A-continued

| Peptide | Sequence | Ki(app)(nM) |
|---------|----------|-------------|
|         | A—Q—S—G—L—G—C—N—S—F—R—Y |  |

Table 1A compares receptor-binding affinity (Ki-(app)) of rANP(126-150) with Ki(app) of cyclic analog peptides wherein, for compounds AP23-25, the pentapeptide core is RIDRI, and the disulfide ring size varies. Also included, as a negative control, is AP54 which lacks a residue of the requisite pentapeptide and is not an invention compound. As shown, it does not bind to the receptor. The data in table IA demonstrate that in the cyclic forms, it is not necessary to include a hydrophobic residue proximal to the pentapeptide core, as in the linear compounds herein. However, as shown below, it may be advantageous to do so. Since receptor binding capacity is substantially diminished for AP54, AP54 should exhibit weaker biological activity if the Ki(app) correlates to activity. This is confirmed in Section B below, compound 25 shown in Table 1A which binds to receptor exhibits in vivo activity in rats, whereas the negative control, AP54, does not.

Correlation of Ki(app) for representative compounds of the invention with in vivo activity is set forth in the description of section B below. AP101, AP319, and AP324 are shown to induce diuresis in rats; AP101, AP306, AP314, and AP324 are shown to cause diuresis in dogs in section B.

TABLE 1B

| Peptide | Sequence | Ki(app)(nM) |
|---------|----------|-------------|
| AP101 | A—F—G—G—R—I—D—R—I—G—A—NH$_2$ | 2.63 |
| AP306 | (2-NA)—G—G—R—I—D—R—I—G—A—NH$_2$ | 2.03 |
| AP314 | (2-NA)—G—G—R—I—D—R—I—NH$_2$ | 14.5 |
| AP319 | (2-NOA)—G—G—R—I—D—R—I—NH$_2$ | 6.0 |
| AP324 | (2-NA)—NH(CH$_2$)$_4$CO—R—I—D—R—I—NH$_2$ | 48.5 |

These results clearly also show that the native upstream peptide containing the phenylalanine residue can be replaced by a hydrophobe spaced at a comparable distance.

Having shown the correlation between Ki(app) and in vivo activity, Ki(app) is shown in the following tables as a measure of activity of a large number of compounds of this invention.

TABLE 1C

| Peptide | Sequence | Ki(app)(nM) |
|---------|----------|-------------|
| rANP (126-150) | R—S—S—C—F—G—G—R—I—D—R—I—G—A—S—Q—G—L—G—C—N—S—F—R—Y | 7.50 |
| AP104 | F—G—G—R—I—D—R—I—G—A—A—NH$_2$ | 2.50 |
| AP102 | A—F—G—G—R—I—D—R—I—G—NH$_2$ | 14.04 |
| AP103 | A—F—G—G—R—I—D—R—I—NH$_2$ | 12.42 |
| AP132 | (desNH$_2$—F)—G—G—R—I—D—R—I—NH$_2$ | 10.15 |
| AP175 | Y—A—F—G—G—R—I—D—R—I—G—A—NH$_2$ | 5.94 |
| AP126 | F—G—G—R—I—D—R—I—G—A—NH$_2$ | 2.16 |
| AP119 | F—G—G—R—I—D—R—I—NH$_2$ | 8.9 |
| AP176 | A—F—G—G—R—I—D—R—I—G—Y—NH$_2$ | 6.65 |
| AP151 | A—F —G—G—R—I—D—R—I—G—A—NH$_2$ | 39.6 |
| AP133 | A—F—A —G—R—I—D—R—I—G—A—NH$_2$ | 2.93 |
| AP157 | A—F—G—A —R—I—D—R—I—G—A—NH$_2$ | 5.90 |
| AP130 | (desNH$_2$—F)—G—G—R—I—D—R—I—G—A—NH$_2$ | 8.8 |
| AP302 | A—F—G—G—R—I —D—R—I—G—A—NH$_2$ | 18.9 |
| AP304 | A—F—G—G—R—I—D—R —I—G—A—NH$_2$ | 95.6 |
| AP305 | A—F—G—G—R—I—D—R—I —G—A—NH$_2$ | 70.62 |
| AP125 | R—I—D—R—I—G—NH$_2$ | >200 |
| AP105 | G—G—R—I—D—R—I—G—A—A—NH$_2$ | >200 |
| AP301 | A—F—G—G—R —I—D—R—I—G—A—NH$_2$ | >200 |
| AP303 | A—F—G—G—R—I—D —R—I—G—A—NH$_2$ | >200 |

The data in Table 1C shows that compounds retaining the hydrophobic F residue proximal to the core pentapeptide retain activity, those not containing a hydrophobic residue upstream, e.g. AP125 and 105, do not.

The data in Table 1D show that the hydrophobic F residue may be replaced by an alternate hydrophobic group and that certain variations within the scope of the invention from the preferred R(1/M)DRI core do not diminish activity.

TABLE 1D

| Peptide | Sequence | Ki(app)(nM) |
|---------|----------|-------------|
| AP307 | (2-NOA)—NH$_2$(CH$_2$)$_4$CO—R—I—D—R—I—NH$_2$ | 39.9 |
| AP309 | (1-AA)—G—G—R—I—D—R—I—NH$_2$ | 30.0 |
| AP311 | (FMOC)—G—G—R—I—D—R—I—NH$_2$ | 10.33 |
| AP312 | (FMOC)—G—G—R—I—D—R—I—G—A—NH$_2$ | 6.27 |
| AP313 | (IP)—G—G—R—I—D—R—I—G—A—NH$_2$ | 4.52 |
| AP316 | (1-NOA)—G—G—R—I—D—R—I—NH$_2$ | 50.4 |
| AP317 | (4-BPA)—G—G—R—I—D—R—I—NH$_2$ | 123.8 |
| AP318 | (2-NOA)—G—G—R—I—D—R—I—G—A—NH$_2$ | 8.7 |
| AP320 | (2-NA)—G—(Sar)—R—I—D—R—I—NH$_2$ | 47.4 |
| AP321 | (2-NA)—G—(Aib)—R—I—D—R—I—NH$_2$ | 33.0 |
| AP322 | (2-NOA)—A —G—R—I—D—R—I—NH$_2$ | >100 |

TABLE 1D-continued

| Peptide | Sequence | Ki(app)(nM) |
|---|---|---|
| AP323 | (FMOC)—NH(CH$_2$)$_4$CO—R—I—D—R—I—NH$_2$ | 162.6 |
| AP325 | (2-NOA)—NH(CH$_2$)$_5$CO—R—I—D—R—I—NH$_2$ | >100 |
| AP327 | (2-NA)—NH(CH$_2$)$_3$CO—R—I—D—R—I—NH$_2$ | 184 |
| AP328 | (2-NA)—G—G—R—I—D—R—I—NH(ethyl) | 19.87 |
| AP329 | (2-NA)—NH(CH$_2$)$_5$CO—R—I—D—R—I—NH$_2$ | 147.78 |
| AP330 | (2-NA)—S—G—R—I—D—R—I—NH$_2$ | 16.4 |
| AP331 | (3-DPP)—G—G—R—I—D—R—I—G—A—NH$_2$ | 6.15 |
| AP334 | (CHA)—G—G—R—I—D—R—I—NH$_2$ | 92.8 |
| AP524 | (2-NA)—G—G—R—I—D—R—I—G—NH-(ethyl) | 2.76 |
| AP525 | (2-NA)—G—G—R—I—D—R—I—G—(Aib)—NH$_2$ | 22.75 |
| AP526 | (2-NA)—G—G—R—I—D—R—I—NH—(CH$_2$)$_4$—CONH$_2$ | 50.5 |
| AP528 | 2(2'-(6'-MeONAP))—G—G—R—I—D—R—I—G—A—NH$_2$ | 22.5 |
| AP530 | (2-NA)—NH(CH$_2$)$_4$CO—R—I—D—R—I—G—NH—(ethyl) | 50.5 |
| AP531 | (3-IB)—G—R—I—D—R—I—G—A—NH$_2$) | 9.34 |
| AP532 | (3-IB)—beta—Ala—R—I—D—R—I—G—A—NH$_2$) | 11.95 |
| AP533 | (bis—(1'-NM)acetyl)—G—G—R—I—D—R—I—G—A—NH$_2$) | 52.0 |
| AP534 | (DBA)—G—G—R—I—D—R—I—G—A—NH$_2$) | 8.81 |
| AP576 | (2-NOA)—NH(CH$_2$)$_3$CO—R—I—D—R—I—G—A—NH$_2$ | 16.0 |
| AP597 | (3-IB)—G—R—I—D—R—I—G—A—NH$_2$ | 9.3 |

All of the foregoing compounds contain the preferred R(I/M)DRI core per se.

| AP332 | (2-NA)—G—G—R—I—D—R—L—NH$_2$ | 44.2 |
|---|---|---|
| AP338 | (2-NA)—G—G—A—I—D—R—I—NH$_2$ | 82.6 |
| AP351 | (2-NA)—G—G—R—I—D—Q—I—NH$_2$ | 20.0 |
| AP518 | (2-NA)—G—G—R—I—E—R—I—NH$_2$ | 38 |
| AP522 | (2-NA)—G—G—Q—I—D—R—I—NH$_2$ | 23.0 |
| AP523 | (2-NA)—G—G—K—I—D—R—I—NH$_2$ | 36.7 |
| AP527 | (2-NA)—G—G—R—Cha—D—R—I—NH$_2$ | 22.5 |
| AP529 | (2-NA)—G—G—R—I—D—R—N—MeIle—G—NH—(ethyl) | 87.3 |
| AP535 | (2-NA)—G—G—R—I—D—R—V —NH$_2$) | 14.0 |
| AP537 | (2-NA)—G—G—R—I—D—R—F —NH$_2$) | >160 |
| AP590 | (2-NA)—G—G—R—tBuA—D—R—I—NH$_2$ | 12.0 |
| AP591 | (2-NA)—G—G—R—tBuG—D—R—I—NH$_2$ | 14.0 |
| AP592 | (2-NA)—G—G—R—I—D—Orn—I—NH$_2$ | 25.0 |
| AP593 | (2-NA)—G—G—R—I—D—Cit—I—NH$_2$ | 55.0 |
| AP594 | (2-NA)—G—G—R—I—D—R—tBuA—NH$_2$ | 15.0 |
| AP595 | (2-NA)—G—G—R—I—D—R—Phg—NH$_2$ | 100.0 |
| AP596 | (2-NA)—G—G—R—I—D—R—NMeIle—NH(ethyl) | 87.3 |
| AP599 | (2-NA)—G—G—R—Cha—D—R—I—NH$_2$ | 22.5 |
| AP333 | (2-NA)—G—G—R—I—D—R—V—NH$_2$ | 106.4 |
| AP536 | (2-NA)—G—G—R—I—D—R—L —NH$_2$) | 106.4 |
| AP512 | (2-NA)—G—G—L—I—D—R—I—NH$_2$ | >160 |
| AP514 | (2-NA)—G—G—Nle—I—D—R—I—NH$_2$ | 267.0 |
| AP515 | (2-NA)—G—G—R—MSO—D—R—I—NH$_2$ | >400 |
| AP516 | (2-NA)—G—G—R—I—D—S—I—NH$_2$ | 399 |
| AP519 | (2-NA)—G—G—R—I—D—R—P—NH$_2$ | >400 |
| AP521 | (2-NA)—G—G—R—F—D—R—I—NH$_2$ | 400 |
| AP575 | (2-NA)—G—G—R—Phg—D—R—I—NH$_2$ | 194.0 |
| AP789 | (2-NOA)—NH—(CH$_2$)$_7$—CO—R—I—D—R—I—NH$_2$ | 380 |

In the compounds above, the $Z_2$ spacer is (AA)$_a$ or HN(CH$_2$)$_m$CO—. In these cases, $Z_3$ is NH$_2$, NHR', or a very short peptide of 1-3 amino acid residues, or an amide or alkyl amide thereof.

Compounds having relatively low activity as judged by Ki are placed at the end of the table. AP512, AP514, AP515, AP516, AP519, AP521 and AP575 have very low, if any, activity. All except AP519 fall outside the invention compounds, as lacking the required pentapeptide core; AP519 is not a preferred embodiment.

Table 1E shows the activity of compounds analogous to those of Table 1D, but with spacers of the formula —(Q)$_m$—B—(Q)$_m$—(CO)$_x$—.

TABLE 1E

| Peptide | Sequence | Ki(app)(nM) |
|---|---|---|
| AP538 | 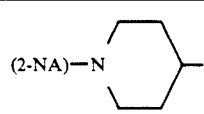 (2-NA)—N⟨hexyl⟩—CO—R—I—D—R—I—NH$_2$ | 9.9 |
| AP539 | 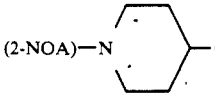 (2-NOA)—N⟨hexyl⟩—CO—R—I—D—R—I—NH$_2$ | 9.1 |

TABLE 1E-continued

| Peptide | Sequence | Ki(app)(nM) |
|---|---|---|
| AP560 | (2-NA)—NH—⟨phenyl⟩—CO—R—I—D—R—I—NH₂ | 68.8 |
| AP562 | (2-NYL)—N⟨piperidine⟩—CO—R—I—D—R—I—NH₂ | 22.4 |
| AP564 | (2-NA)—NH—⟨phenyl⟩—CH₂CO—R—I—D—R—I—NH₂ | 10.1 |
| AP568 | (2-NA)—NHCH₂—⟨phenyl⟩—CO—R—I—D—R—I—NH₂ | 12.5 |
| AP574 | (2-NYL)—CH₂—N⟨piperidine⟩—CO—R—I—D—R—I—NH₂ | 26.5 |
| AP704 | (2-NA)—N⟨piperidine⟩—CH₂—R—I—D—R—I—NH₂ | 17.0 |
| AP790 | (2-NYL)—NH—⟨phenyl⟩—CH₂—CO—R—I—D—R—I—NH₂ | 5.2 |
| AP791 | (2-NOA)—NH—⟨phenyl⟩—CO—R—I—D—R—I—NH₂ | 31.1 |
| AP792 | (2-NOA)—NH—⟨phenyl⟩—CH₂—CO—R—I—D—R—I—NH₂ | 6.3 |
| AP793 | (2-NOA)—N⟨piperidine⟩—CO—R—I—D—R—I—NH₂ | 76.8 |
| AP794 | (2-NYL)—CH₂NH—⟨phenyl⟩—CO—R—I—D—R—I—NH₂ | 13.1 |
| AP795 | (2-NYL)—NHCH₂—⟨phenyl⟩—CO—R—I—D—R—I—NH₂ | 11.9 |
| AP796 | (2-NL)—CH₂CH₂NH—⟨phenyl⟩—CH₂—CO—R—I—D—R—I—NH₂ | 27.3 |

TABLE 1E-continued

| Peptide | Sequence | Ki(app)(nM) |
|---|---|---|
| AP816 | (2-NOA)—NH—⟨C6H4⟩—CH2(CH2NH)—R—I—D—R—I—NH2 | 17.4 |
| AP817 | (2-ClPA)—NH—⟨C6H4⟩—CH2CO—R—I—D—R—I—NH2 | 21.1 |
| AP818 | (2-BrPA)—NH—⟨C6H4⟩—CH2CO—R—I—D—R—I—NH2 | 20.5 |
| AP819 | (2-BrAF)—NH—⟨C6H4⟩—CH2CO—R—I—D—R—I—NH2 | 3.8 |

Table 1F shows compounds similar to those of Table 1E except that the core R(I/M)DRI sequence contains at least one substitution, preferably K or (Acetyl) Lys rather than R, or L rather than (I/M).

TABLE 1F

| Peptide | Sequence | Ki(app)(nM) |
|---|---|---|
| AP798 | (2-NOA)—NH—⟨C6H4⟩—CH2—CO—K—I—D—R—I—NH2 | 3.95 |
| AP799 | (2-NA)—NH—⟨C6H4⟩—CH2CO—R—I—D—K—I—NH2 | 3.6 |
| AP800 | (2-NA)—NH—⟨C6H4⟩—CH2—CO—K—I—D—R—I—NH2 | 2.90 |
| AP801 | (2-NOA)—NH—⟨C6H4⟩—CH2—CO—(Acetyl)Lys—I—D—R—I—NH2 | 3.95 |
| AP802 | (2-NYL)—NH—⟨C6H4⟩—CH2CO—K—I—D—R—I—NH2 | 8.7 |
| AP809 | (2-NYL)—NH—⟨C6H4⟩—CH2CO—K(CH2NH)—I—D—R—I—NH2 | 14.7 |
| AP814 | (2-NYL)—NH—⟨C6H4⟩—CH2CO—K(CH2NH)—I—D—R—NH—(S)—2-methylbutyl | 33.0 |
| AP815 | (2-NOA)—NH—⟨C6H4⟩—CH2CO—Orn—I—D—R—I—NH2 | 10.0 |

Table 1G shows the results for compounds which have non-peptide bond linkages in the core sequence, but contain otherwise unmodified R(I/M)DRI; or have only one other modification therein.

TABLE 1G

| Peptide | Sequence | Ki(app)(nM) |
|---|---|---|
| AP701 | (2-NA)—NH—⌬—CH$_2$CO—R—I(CH$_2$NH)D—R—I—NH$_2$ | 60.3 |
| AP806 | (2-NA)—NH—⌬—CH$_2$CO—K(CH$_2$NH)I—D—R—I—NH$_2$ | 14.0 |
| AP807 | (2-NA)—NH—⌬—CH$_2$—CO—R—I—D—K(CH$_2$NH)I—NH$_2$ | 112 |
| AP808 | (2-NOA)—NH—⌬—CH$_2$CO—K(CH$_2$NH)I—D—R—I—NH$_2$ | 98.9 |

Table 1H shows the activity of embodiments wherein $A_{12}$ is a covalent bond; other modifications may also apply.

TABLE 1H

| Peptide | Sequence | Ki(app)(nM) |
|---|---|---|
| AP509 | (2-NOA)—G—G—R—I—D—R—NH—CH$_2$—CH(CH$_3$)$_2$ | 120.0 |
| AP510 | (2-NA)—G—G—R—I—D—R—NH—CH$_2$—CH(CH$_3$)$_2$ | 116.0 |
| AP511 | (2-NA)—G—G—R—I—D—R—NH—CH$_2$—CH(CH$_3$)CH$_3$CH$_3$ | 84.7 |
| AP557 | (2-NA)—N⌬—CO—R—I—D—R—NH—CH$_2$—CH(CH$_3$)CH$_2$CH$_3$ | 41.7 |
| AP810 | (2-NOA)—N⌬—CO—R—I—D—R—NH—(S)—2-methylbutyl | 14.1 |
| AP811 | (2-NYL)—NH—⌬—CH$_2$CO—R—I—D—R—NH—(S)—2-methylbutyl | 2.52 |
| AP812 | (2-NOA)—N⌬—CH$_2$NH—R—I—D—R—NH—(S)—2-methylbutyl | 32.0 |
| AP813 | (2-NOA)—NH—⌬—CH$_2$CO—R—I—D—R—NH—(S)—2-methylbutyl | 56.0 |

These data indicate the Ile at $A_{12}$ is not essential for activity if $Z_3$ is NHR', wherein R' is alkyl, in the foregoing examples, of 4–5C.

In order to show that the receptor binding assay is specific to ANP, data which compares ANP-receptor interactions of rANP(126-150) with the unrelated peptide hormones angiotensin II, glucagon, parathyroid hormone and gamma-MSH is shown:

| Peptide | Ki(app) |
|---|---|
| rANP(126-150) | 7.50 |
| angiotensin II | >500 |
| glucagon | >500 |
| parathyroid hormone | >500 |
| gamma-MSH | >500 |

As shown above, only rANP(126-150) displays detectable ANP-receptor affinity This attests to the relevant ANP-specificity of this receptor.

The data in the foregoing tables show that a large representative sample of the compounds of the invention demonstrate affinity in the specific receptor-binding assay described. The following subsections demonstrate that representative compounds, which demonstrate receptor binding, are also active in vivo, whereas compounds which do not bind to these receptors appear inactive.

B. Whole mammal bioassays

The biological activity of analog compounds o the present invention can be demonstrated in anesthetized rats and dogs. The correlation of receptor binding affinity and in vivo effects demonstrates the predictive value of the receptor assays for biological activity.

1. Diuresis in anesthetized rats

In one set of examples, cannulae were placed in the left and right ureters and femoral vein of anesthetized rats and urine was collected from the ureters. Analog peptides were administered via the femoral vein. Prior to infusing the analog peptides, saline was infused for 30 minutes, urine was collected for 6 five-minute baseline periods and urine volume was determined gravimetrically.

Following these baseline collection periods, various analog peptides were infused for 30 or 60 minutes and urine volume was measured in five-minute periods during infusion and for 60 minutes following infusion (at which time rats were returned to saline). Data was examined by averaging urine flow rates for six five-minute baseline control periods immediately preceding infusion, and comparing values during and after administration of peptides with the "baseline" control values. Responses to peptides are thus evaluated and plotted as the percent of baseline control responses. Specific examples are shown in FIGS. 3A–H. The error bars at the beginning of the graphs represent baseline values +standard deviations. Responses to peptides that are substantially above baseline ±SD can thus be interpreted as being statistically significant increases.

As shown in FIG. 3A–H, diuretic responses correlate with predictions from receptor-binding studies. Analog peptides AP25, AP20, AP21, AP37, AP101, AP319 and AP324, significantly increased urine flow rate (urine volume) when infused at 5 mcg/min, 5 mcg/min, 5 mcg/min, 10 mcg/min, 5 mcg/min, 10 mcg/min and 10 mcg/min respectively. Their respective Ki values are 8.62, 7.50, 15.15, 13.40, 2.63, and 6.0. (AP20 and AP21 are cyclic analogs not within the scope of the present invention.)

On the other hand, AP54, which falls outside the scope of the compounds of the invention, and which was shown in Table 1A to lack significant receptor-binding activity, also appears inactive in vivo. These data, therefore, demonstrate the appropriate correlation between receptor-binding activity and in vivo activity.

2. Diuresis and natriuresis in anesthetized dogs

The biological activity of analog compounds of the present invention can also be demonstrated in pentobarbital-anesthetized dogs. In these examples, cannulae were placed in the left and right ureters and femoral vein of anesthetized dogs and urine was collected from the ureters. Analog peptides were administered via the femoral vein. Prior to infusing analog peptides, saline was infused for 30 minutes and urine was then collected for three ten-minute collection periods. Urine volume was determined gravimetrically and urine sodium was determined photometrically.

Following these three baseline collection periods, the selected analog peptides were infused for 60 minutes and urinary flow was measured for an additional 60 minutes following infusion. During infusion (60 minutes) and recovery (60 minutes), ten-minute collection periods were obtained. Control animals which received only saline were studied in parallel.

Data were examined by comparing urine flow rates for dogs infused with peptides AP101 (3 mcg/kg/min), AP306 (3 mcg/kg/min), AP324 (3 mcg/kg/min), or AP314 (1 mcg/kg/min) against control animals infused with saline.

TABLE 2A

| Peptide | Dose (mcg/kg/min) | Peak Urine Flow Rate V (ml/min) | Peak Urine Sodium Excretion $U_{Na}$ V (mcEq/min) | Ki |
|---|---|---|---|---|
| Control | — | 0.61 | 40 | |
| AP101 | 3 | 1.77* | | 2.63 |
| AP306 | 3 | 2.09* | | 2.03 |
| AP314 | 1 | 2.05* | 365* | 14.5 |
| AP324 | 3 | 2.47* | 495* | 48.5 |

As shown in Table 2A, the peak in vivo responses to the peptides are substantially above baseline (*P<0.05 by Student's test) and are interpreted as being statistically significant increases, comparable to the effects of native ANP compounds.

Diuretic and natriuretic responses to peptides AP101, AP306, AP314 and AP324 correlate with predictions from receptor-binding assays. Analog peptides AP101, AP306, AP314 and AP324, each of which is a small linear peptide with substantial Ki(app)s (Table 1B), significantly increased urine flow rate (urine volume) and urinary sodium excretion when infused at 3, 3, 1 or 3 mcg/kg/minute, respectively. Thus, these analog peptides are shown to each induce diuresis and natriuresis and therefore support the predictive value of the receptor-binding analysis for diuretic potency.

3. Blood pressure responses in anesthetized rats

Compounds which are cyclic analogs of ANP also lowered blood pressure when administered as a bolus or infusion to anesthetized rats. Table 2B presents data which compares the blood pressure effects of representative analog peptides AP20 and AP37, with that of rANP(126–150), following administration by infusion.

TABLE 2B

| Peptide | Structure | Dose (p mol/kg/min) | Blood Pressure |
|---|---|---|---|
| rANP (126–150) | R—S—S—C—F—G—G— R—I—D—R—I—G—A—Q— S—G—L—G—C—N—S—F—R—Y | 183 | −39 ± 5 |
| AP20 | R—S—S—C—F—G—G— R—I—D—R—I—G—A— C—N—S—F—R—Y | 733 | −34 ± 3 |
| AP37 | C—F—G—G—R—I—D— R—I—G—A—C—NH$_2$ | 7330 | −14 ± 3 |

As shown, each of the analog peptides lowered blood pressure significantly. While analog peptide AP37 exhibited a weaker effect on blood pressure at a substantially higher dose (40x that of rANP(126–150)), it nevertheless was hypotensive.

Again, compounds which showed receptor-binding affinity are shown to be active in vivo. The correlation between the in vitro receptor-binding test and in vivo results further supports the validity of the receptor-binding assay to show the therapeutic efficacy of the compounds tested.

Thus, the administration to mammalian hosts of therapeutically effective amounts of analog peptides, or pharmaceutical compositions containing these analog peptides, can be used to substantially increase natriuresis and diuresis and/or alter the vascular caliber. Furthermore, administration of selected analog peptides can be used to treat cases of hypertension or various edematous states whose etiology does not require the full range of biological activity provided by native ANP compounds.

C. Isolated Tissue Bioassays

It is believed, as stated above, that the effect of the analogs of the invention herein in vivo is due to their ability to potentiate the effect of endogenous ANP, possibly through blockage of the receptors involved in binding and clearing endogenous ANPs. Accordingly, one would expect that the diuretic and natriuretic effects of the analogs would be diminished or eliminated in isolated tissue where ANPs are not present unless specifically supplied. The results below demonstrate support for this theoretical model. As shown below, while a representative analog, AP57 (not within the scope of the invention—a cyclic analog), was active in vivo, it was not active in isolated perfused rat kidney. However, in the same model system, it was able to potentiate the effect of rANP(123-150).

AP57 has the sequence R-S-S-C-F-G-G-R-I-D-R-I-G-A-C-NH$_2$ and shows a K$_i$ of 8.2. rANP(123-150) has the sequence of ANP(126-150) which includes 3 additional upstream amino acids of the naturally occurring peptide.

1. Natriuresis and diuresis in the isolated perfused rat kidney

The biological actions of the ANP analogs can be demonstrated in the isolated perfused rat kidney, as described in Camargo, M. J. F., et al, Am J Physiol (1984) 246:F447-F456. In a particular set of examples, the effect of the 15-amino-acid peptide AP57 at a concentration of $10^{-7}$ M, was demonstrated in the intact kidney. The results are in Table 2C.

TABLE 2C

EFFECT OF AP57 ON DOSE-RESPONSE CURVES OF rANP(123-150) IN THE ISOLATED PERFUSED RAT KIDNEY

| | GFR (ml/min) | FF (%) | RVR (mmHg/ml/min) | U$_{Na}$V (uEq/min) | FE$_{Na}$ (%) | V (ul/min) |
|---|---|---|---|---|---|---|
| A. CONTROL KIDNEYS (N=5) | | | | | | |
| | 0.48 ± 0.06 | 1.21 ± 0.15 | 2.30 ± 0.12 | 0.37 ± 0.08 | 0.56 ± 0.09 | 16.5 ± 2.0 |
| B. AP57 ($10^{-7}$ M) (N=4) | | | | | | |
| | 0.55 ± 0.07 | 1.37 ± 0.22 | 2.27 ± 0.17 | 0.17 ± 0.04 | 0.24 ± 0.08 | 13.8 ± 2.0 |
| C. rANP(123-150) ($10^{-11}$ TO $10^{-8}$ M) (N=4) | | | | | | |
| [C] | 0.45 ± 0.06 | 1.22 ± 0.20 | 2.29 ± 0.15 | 0.30 ± 0.05 | 0.50 ± 0.10 | 15.0 ± 1.8 |
| $10^{-11}$ | 0.53 ± 0.04 | 1.33 ± 0.20 | 2.36 ± 0.20 | 0.53 ± 0.14 | 0.72 ± 0.19 | 21.8 ± 1.7 |
| $10^{-10}$ | 0.66 ± 0.07 | 1.76 ± 0.29 | 2.51 ± 0.26 | 1.13 ± 0.43 | 1.21 ± 0.44 | 35.5 ± 5.7 |
| $10^{-9}$ | 0.82 ± 0.07 | 2.30 ± 0.41 | 2.64 ± 0.35 | 3.22 ± 0.92 | 2.78 ± 0.89 | 74.0 ± 14.8 |
| $10^{-8}$ | 0.80 ± 0.08 | 2.23 ± 0.44 | 2.66 ± 0.32 | 4.78 ± 1.15 | 4.12 ± 0.94 | 96.6 ± 24.0 |
| D. rANP(123-150) ($10^{-11}$ TO $10^{-8}$ M) IN PRESENCE OF AP57 ($10^{-7}$ M)$^3$ (N=4) | | | | | | |
| [C] | 0.65 ± 0.06 | 1.57 ± 0.27 | 2.21 ± 0.21 | 0.17 ± 0.05 | 0.18 ± 0.04 | 16.3 ± 2.0 |
| $10^{-11}$ | 0.80 ± 0.08 | 2.04 ± 0.15 | 2.50 ± 0.15 | 0.45 ± 0.10 | 0.41 ± 0.11 | 31.0 ± 3.7 |
| $10^{-10}$ | 0.93 ± 0.04 | 2.65 ± 0.20 | 2.80 ± 0.31 | 1.76 ± 0.25 | 1.33 ± 0.20 | 70.6 ± 4.2 |
| $10^{-9}$ | 0.99 ± 0.07 | 2.81 ± 0.40 | 2.79 ± 0.34 | 6.03 ± 1.37 | 4.08 ± 0.72 | 139 ± 14 |
| $10^{-8}$ | 0.84 ± 0.13 | 2.30 ± 0.47 | 2.63 ± 0.33 | 6.47 ± 2.29 | 4.77 ± 1.22 | 132 ± 33 |

GFR=glomerular filtration rate; FF=filtration fraction; RVR=renal vascular resistance; U$_{Na}$V=urinary sodium excretion rate; FE$_{Na}$=fractional sodium excretion; V=urine flow rate.
Results are presented as mean ± SE, with the number of kidneys presented for each test phase. In the phase demonstrating the effect of AP57 on the dose response curve of rANP(123-150), $10^{-7}$ M AP57 was added 30 minutes before the addition of increasing doses of rANP(123-150).

Despite having natriuretic and diuretic activities in an intact rat, analog peptide AP57 was not active in the isolated perfused rat kidney at a concentration of $10^{-7}$ M, as compared to rANP(123-150)-, as shown in sections A and B of the table.

Sections C and D of the table show the ability of peptide AP57 to modulate the renal responses to rANP(123-550). As shown in Table 2C, section C, rANP(123-150) increases glomerular filtration rate, renal vascular resistance, filtration fraction, urinary sodium excretion rate, fractional excretion of sodium and urinary flow rate in a dose-dependent manner in the concentration range from $10^{-11}$ to $10^{-7}$ M. Table 2C, section D, shows that pretreatment of the isolated kidney with $10^{-7}$ M AP57 causes the subsequent responses to rANP(123-150) to occur at reduced concentrations. Analog peptide AP57, despite being apparently inactive in this in vitro model, increased the potency of rANP(1-23-150). Subsequent assays have confirmed these observations and conclusions.

Table 2D shows that both rANP(123-150) and AP57 compete for specific ($^{125}$I)-rANP(123-150) binding to the cortex of the kidney.

TABLE 2D

RATIO OF BOUND/FREE ($^{125}$I)-rANP(123-150)·

| | Whole Kidney | Outer Cortex |
|---|---|---|
| ($^{125}$I)-rANP(123-150) (4 × $10^{-12}$ M) (n=3) | 122 ± 46 | 176 ± 23 |
| ($^{125}$I)-rANP(123-150) (4 × $10^{-12}$ M) + rANP(123-150) ($10^{-7}$ M) (n=3) | 0.63 ± 0.27 | 0.77 ± 0.30 |
| ($^{125}$I)-rANP(123-150) (4 × $10^{-12}$ M) + AP57 ($10^{-7}$ M) | 1.27 ± 0.32 | 1.68 ± 0.44 |

TABLE 2D-continued

| RATIO OF BOUND/FREE ($^{125}$I)-rANP(123-150) | |
|---|---|
| Whole Kidney | Outer Cortex |
| (n = 3) | |

These cortical-associated receptor sites may be involved in the clearance and removal of the ANPs. Thus, AP57 may block the clearance of rANP(123-150) in the isolated kidney model, thereby explaining its ability to potentiate the effects of rANP(123-150). Furthermore, if AP57 blocks clearance of endogenous ANPs, it may explain the natriuretic, diuretic and vasorelaxant responses to these peptides in vivo.

Although the foregoing invention has been illustrated above for purposes of aiding understanding, modifications of the invention may be practiced while remaining within the spirit and scope of the appended claims.

We claim:

1. A linear peptide compound having natriuretic, diuretic and/or vasodilator activity in mammals, which has the formula:

$$Z_1Z_2\text{-}AA_8\text{-}AA_9\text{-}AA_{10}\text{-}AA_{11}\text{-}AA_{12}\text{-}Z_3 \quad (1)$$

wherein:
each of $AA_8$ and $AA_{11}$ is, independently, a basic/non-cyclic; neutral/nonpolar/small; or neutral/polar/large/nonaromatic amino acid residue; and $AA_8$ can also be a neutral nonpolar/large/nonaromatic amino acid residue;

$AA_9$ is a neutral/nonpolar/large/nonaromatic amino acid residue in the D or L configuration;

$AA_{10}$ is an acidic amino acid residue;

$AA_{12}$ is a neutral/nonpolar/large/nonaromatic amino acid residue in the D or L configuration or a covalent bond; and wherein $Z_1$ is a peptide of from 1 to 125 amino acids having as its carboxy-terminal residue a hydrophobic amino acid residue, or the desNH$_2$ form thereof, or is a hydrophobic aliphatic, aromatic, or mixed aliphatic/aromatic organic group of from 6 to 20 carbon atoms;

$Z_2$ is a spacer group capable of providing a spaced dimension of 4.5-15 angstroms between $AA_8$ and the hydrophobic moiety of $Z_1$;

$Z_3$ is (OH), NH$_2$, NHR' or NR'R'' wherein R' or R'' are each independently straight or branched chain alkyl of 1-10 carbon atoms wherein 1 or 2 carbons may be replaced by O, N, or S; or is a peptide of 1-20 amino acid residues, or an amide or alkyl amide thereof; but when $AA_{12}$ is a covalent bond, $Z_3$ cannot be (OH), NH$_2$ or a peptide; and wherein one or more of the amide linkages between adjacent amino acid residues may optionally be replaced by a linkage selected from the group consisting of —CH$_2$NH—, —CH$_2$S—, —CH$_2$CH$_2$—, —CH=CH—, —COCH$_2$—, —CH(OH)CH$_2$— and —CH$_2$SO—, with the proviso that if $AA_8$-$AA_{12}$ is R-M-D-R-I, and $Z_3$ is G-A-Q-S-G-L-G, $Z_1Z_2$ cannot be F-G-G; and with the additional proviso that if $AA_8$-$AA_{12}$ is R-I-D-R-I, and $Z_3$ is G-A-Q-S-G-L-G-C-N-S-F-R, $Z_1Z_2$ cannot be F-F-G.

2. The compound of claim 1 wherein $Z_1$ is selected from the group consisting of 9-fluorenylmethyloxycarbonyl, benzyloxycarbonyl, 2-(2'-(6'-methoxy naphthyl))propionyl, diphenylpropionyl, biphenylacetyl, 3,3,3-triphenylpropionyl, cyclohexylacetyl, 3-indolepropionyl, 4-indolebutyryl, 1-adamantylacetyl, 1-naphthylacetyl, 2-naphthylacetyl, 1-naphthoxyacetyl, 2-naphthoxyacetyl, dibenzylacetyl, bis (1'-napthylmethyl) acetyl, 2-naphthyl thioacetyl, 3-phenoxypropionyl, 2-naphthoyl, 2-naphthoxy, 2-naphthyl, phenylalanyl, des-NH$_2$ phenylalanyl, 2-halo phenylacetyl and 2-halo acetyl phenylalanyl.

3. The compound of claim 2 wherein $Z_1$ is selected from the group consisting of 2-naphthylacetyl, 2-naphthoxyacetyl, 1-naphthylacetyl, phenylalanyl and des-NH$_2$ phenylalanyl.

4. The compound of claim 1 wherein $Z_2$ is selected from the group consisting of
(a) -(AA)$_a$- wherein AA is an amino acid and a is 1 or 2;
(b) -(P)$_n$-(CO)-$_x$ wherein x is 0 or 1, n is 1-6, and P is CH$_2$ wherein 1-2 of said —CH$_2$— groups can be replaced by NH, provided N-N does not occur; and
(c) -(Q)$_m$-B-(Q)$_m$-(CO)$_x$- wherein x is 0 or 1, each m is 0-3, wherein the sum of m is 5 or less, -B- is a saturated or unsaturated five- or six-membered ring optionally containing an N heteroatom, and Q is CH$_2$ or NH, provided —N—N— does not occur.

5. The compound of claim 4 wherein $Z_2$ is 4-APA.

6. The compound of claim 1 wherein $Z_3$ is NH$_2$ or NHR', or a peptide of 1-2 amino acid residues or the amide or alkyl amide form thereof.

7. The compound of claim 6 wherein R' is (S)-2-methylbutyl.

8. The compound of claim 1 wherein $AA_8$-$AA_9$-$AA_{10}$-$AA_{11}$-$AA_{12}$ is R(I/M)DRI or at most one residue therein is replaced by substituting
K, (NeAcetyl) Lys, A, Q, N, L or NMeIle for R as $AA_8$;
V, V , L, L , I , M , t-BuA, t-BuG or Cha for I or M as $AA_9$;
E for D as $A_{10}$;
K, (Acetyl) Lys, A, Q, N, Orn or Cit for R as $AA_{11}$; and
M, M , V V , L, L , I , P, N-MeIle, t-BuA or a covalent bond for I as $AA_{12}$.

9. The compound of claim 1 wherein $AA_8$-$AA_9$-$AA_{10}$-$AA_{11}$-$AA_{12}$ is selected from the group consisting of:

| A(I/M)DRI | RM DRI | R(I/M)DRL |
|---|---|---|
| K(I/M)DRI | RLDRI | R(I/M)DRM |
| (Ne Acetyl) Lys (I/M)DRI | | |
| Q(I/M)DRI | R(I/M)ERI | R(I/M)DRM |
| RVDRI | R(I/M)DKI | R(I/M)DRI |
| RI DRI | R(I/M)DQI | R(I/M)DRV and |
| R(I/M)DRI | | |

10. The compound of claim 9 wherein $AA_8$-$AA_9$-$AA_{10}$-$AA_{11}$-$AA_{12}$ is K(I/M)DRI, NeAcetyl Lys (I/M)-DRI, R(I/M)DKI, or R(I/M)DRI.

11. The compound of claim 1 wherein $AA_8$-$AA_9$-$AA_{10}$-$AA_{11}$-$AA_{12}$ $Z_3$ is R(I/M)DR-NHR, 12. The compound of claim 11 wherein R' is (S)-2-methylbutyl.

13. The compound of claim 1 wherein at least one of the amide linkages between adjacent amino acid residues is replaced by a linkage selected from the group consisting of —CH$_2$NH—, —CH$_2$S—, —CH$_2$CH$_2$—, —CH=CH— (cis and trans), —COCH$_2$—, —CH(OH)CH$_2$— and —CH$_2$SO—.

14. The compound of claim 10 wherein one peptide linkage is replaced by CH$_2$NH—.

15. The compound of claim 1 which is selected from the group consisting of the compounds set forth in FIG. 4 herein.

16. A composition useful as a natriuretic, diuretic and/or vasodilator comprising a therapeutically effective amount of the compound of claim 1 together with a pharmaceutically acceptable carrier.

17. A method for inducing natriuresis, diuresis, or vasodilatation in a mammalian host, which comprises administering to said host a pharmaceutically effective amount of the composition of claim 16.

18. A process for production of a peptide compound having natriuretic, diuretic and/or vasodilator activity in mammals, said peptide compound having the formula of the compound of claim 1, or the pharmacologically acceptable salts thereof, which process comprises the following steps:

a. preparing a protected peptide bonded to a solid resin carrier in a reaction mixture, wherein the peptide has an amino acid sequence as recited above;

b. removing the solid resin carrier from the peptide and deprotecting the peptide;

c. optionally modifying the peptide to add any desired organic substituent groups as recited above; and d. isolating the peptide from any reaction mixture, and optionally, converting the polypeptide into an acid addition salt thereof.

19. The compound of claim 14 wherein said —CH$_2$NH$_2$— linkage replaces the peptide linkage between AA$_8$-AA$_9$ or AA$_9$-AA$_{10}$ or AA$_{11}$-AA$_{12}$.

20. The compound of claim 1 wherein the peptide of Z$_1$ is selected from the group consisting of F, F , AF, YAF and desNH$_2$F.

* * * * *